(12) United States Patent
Towns et al.

(10) Patent No.: US 9,419,233 B2
(45) Date of Patent: Aug. 16, 2016

(54) POLYMERS, THEIR PREPARATION AND USES

(71) Applicants: CAMBRIDGE DISPLAY TECHNOLOGY LIMITED, Cambridgeshire (GB); Cambridge Enterprise Limited, Cambridge (GB)

(72) Inventors: Carl R. Towns, Cambridgeshire (GB); Chris Mak, Cambridge (GB); Khai Leok Chan, Cambridge (GB); Andrew Bruce Holmes, Parkville (AU)

(73) Assignees: CAMBRIDGE DISPLAY TECHNOLOGY LIMITED, Cambridgeshire (GB); CAMBRIDGE ENTERPRISE LIMITED, Cambridge (GB)

(*) Notice: Subject to any disclaimer, the term of this patent is extended or adjusted under 35 U.S.C. 154(b) by 272 days.

(21) Appl. No.: 13/889,308

(22) Filed: May 7, 2013

(65) Prior Publication Data

US 2013/0334505 A1 Dec. 19, 2013

Related U.S. Application Data

(63) Continuation of application No. 10/578,895, filed as application No. PCT/GB2004/004754 on Nov. 10, 2004, now abandoned.

(30) Foreign Application Priority Data

Nov. 10, 2003 (GB) .................................. 0326138.5
Jun. 14, 2004 (GB) .................................. 0413205.6

(51) Int. Cl.
*H01L 51/50* (2006.01)
*H01L 51/00* (2006.01)
(Continued)

(52) U.S. Cl.
CPC .......... *H01L 51/0094* (2013.01); *C07F 7/0818* (2013.01); *C08G 61/123* (2013.01)

(58) Field of Classification Search
None
See application file for complete search history.

(56) References Cited

U.S. PATENT DOCUMENTS 4,539,507 A 9/1985 VanSlyke et al.
5,150,006 A 9/1992 Van Slyke et al.
(Continued)

FOREIGN PATENT DOCUMENTS

EP 0 880 303 A1 11/1998
EP 0 901 176 A2 3/1999
(Continued)

OTHER PUBLICATIONS

Baldo et al., "Highly Efficient Phosphorescent Emission from Organic Electroluminescent Devices", Nature, vol. 395, pp. 151-154 (1998).
(Continued)

*Primary Examiner* — Gregory Clark
(74) *Attorney, Agent, or Firm* — Marshall, Gerstein & Borun LLP

(57) ABSTRACT

A polymer containing an optionally substituted repeat unit of formula (I) wherein each R is the same or different and represents H or an electron withdrawing group, and each $R^1$ is the same or different and represents a substituent.

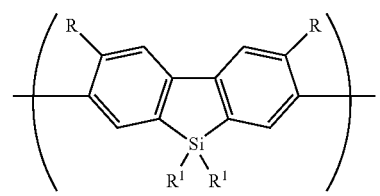

9 Claims, 5 Drawing Sheets

(51) Int. Cl.
*C07F 7/08* (2006.01)
*C08G 61/12* (2006.01)

(56) References Cited

U.S. PATENT DOCUMENTS

| | | | |
|---|---|---|---|
| 5,432,014 | A | 7/1995 | Sano et al. |
| 5,723,873 | A | 3/1998 | Yang |
| 5,798,170 | A | 8/1998 | Zhang et al. |
| 6,083,634 | A | 7/2000 | Shi |
| 6,329,082 | B1 | 12/2001 | Kreuder et al. |
| 6,353,083 | B1 | 3/2002 | Inbasekaran et al. |
| 6,953,628 | B2 | 10/2005 | Kamatani et al. |
| 7,030,138 | B2 | 4/2006 | Fujimoto et al. |
| 2002/0117662 | A1 | 8/2002 | Nii |
| 2002/0182441 | A1 | 12/2002 | Lamansky et al. |
| 2003/0068526 | A1 | 4/2003 | Kamatani et al. |
| 2003/0168656 | A1* | 9/2003 | Kobayashi et al. .............. 257/40 |
| 2003/0186080 | A1 | 10/2003 | Kamatani et al. |
| 2004/0062930 | A1 | 4/2004 | Roberts et al. |
| 2004/0138455 | A1 | 7/2004 | Stossel et al. |
| 2004/0170863 | A1* | 9/2004 | Kim et al. ..................... 428/690 |
| 2004/0219388 | A1 | 11/2004 | Noguchi et al. |

FOREIGN PATENT DOCUMENTS

| | | | |
|---|---|---|---|
| EP | 0 947 123 B1 | | 10/1999 |
| EP | 1 120 839 A2 | | 8/2001 |
| EP | 1 143 538 | | 10/2001 |
| EP | 1 245 659 A1 | | 10/2002 |
| EP | 1 318 163 A1 | | 6/2003 |
| JP | 2000-252065 A | | 9/2000 |
| JP | 2001-181618 | * | 7/2001 ............. C09K 11/06 |
| JP | 2002-324679 | | 11/2002 |
| JP | 2003-206289 | | 7/2003 |
| WO | WO-90/13148 | | 11/1990 |
| WO | WO-96/20253 A1 | | 7/1996 |
| WO | WO-98/10621 | | 3/1998 |
| WO | WO-98/57381 | | 12/1998 |
| WO | WO-99/21935 | | 5/1999 |
| WO | WO-99/48160 | | 9/1999 |
| WO | WO-99/54936 | | 10/1999 |
| WO | WO-00/46321 A1 | | 8/2000 |
| WO | WO-00/48258 | | 8/2000 |
| WO | WO-00/53656 | | 9/2000 |
| WO | WO-00/55927 | | 9/2000 |
| WO | WO-01/62869 | | 8/2001 |
| WO | WO-02/31896 | | 4/2002 |
| WO | WO-02/44189 | | 6/2002 |
| WO | WO-02/45466 | | 6/2002 |
| WO | WO-02/066552 A1 | | 8/2002 |
| WO | WO-02/068435 | | 9/2002 |
| WO | WO-02/081448 | | 10/2002 |
| WO | WO-02/084759 | | 10/2002 |
| WO | WO-03/000821 A1 | | 1/2003 |
| WO | WO-03/018653 | | 3/2003 |
| WO | WO-03/022908 | | 3/2003 |

OTHER PUBLICATIONS

Baldo et al., "Phosphorescent Materials for Application to Organic Light Emitting Devices", Pure Appl. Chem., vol. 71, No. 11, pp. 2095-2106 (1999).

Bernius et al., "Progress With Light-Emitting Polymers", Adv. Mater 12, No. 23, pp. 1737-1750 (2000).

Brunner et al., "Carbazole Compounds as Host Materials for Triplet Emitters in Organic Light-Emitting Diodes: Tuning the HOMO Level Without Influencing the Triplet Energy in Small Molecules",J. Am. Chem. Soc. 126,pp. 6035-6042 (2004).

Chen et al. "Recent Developments in Molecular Organic Electroluminescent Materials", Macromol. Symp. 125, pp. 1-48 (1997).

Dijken et al.,"Carbazole Compounds as Host Materials for Triplet Emitters in Organic Light-Emitting Diodes: Polymer Hosts for High-Efficiency Light-Emitting Diodes", J. Am. Chem. Soc. 126, pp. 7718-7727 (2004).

Hung et al., "Recent Progress of Molecular Organic Electroluminescent Materials and Devices",Materials Science and Engineering R 39,pp. 143-222 (2002).

Kobayashi et al., "A Novel RGB Multicolor Light-Emitting Polymer Display", Synthetic Metals 111-112, pp. 125-128 (2000).

Kabir et al., "Synthesis of Biphenylenes and Tetra[jemu;emes Isomg Copper-Catalyzed Coupling of Arylzinc Intermediates," J. Chem. Soc. Perkins Transactions 1:159-164 (2001).

Kreyenschmidt et al., Thermally Stable Blue-Light-Emitting Copolymers of Poly(alkylfluorene), Macromolecules 31, pp. 1099-1103 (1998).

Müller et al., "Multi-Colour Organic Light-Emitting Displays by Solution Processing", Nature vol. 421, pp. 829-833 (2003).

Niu et al., "Thermal Annealing Below the Glass Transition Temperature: A General Way to Increase Performance of Light-Emitting Diodes Based on Copolyfluorenes", Applied Physics Letters, vol. 81, No. 4, pp. 634-636 (2002).

Patrick et al., "Anti-Pneumocystis Carinii Pneumonia Activity of Dicationic Carbazoles", Eur. J. Med. Chem 32, pp. 781-793 (1997).

Tang et al., "Electroluminescence of Doped Organic Thin Films", J. Appl. Phys. 85 (9), pp. 3610-3616 (1989).

Thompson et al., "Electrophosphorescent Organic Light Emitting Diodes", Polymeric Materials Science & Engineering 83, pp. 202-203 ( 2000).

Yamaguchi et al., "Effects of B and C on the Ordering of L10-CoPt Thin Films", Applied Physics Letters, vol. 79, No. 13, pp. 2001-2003 (2001).

Wu et al., "Convergent Synthetic Routes to Orthogonally Fused Conjugated Oligomers Directed Toward Molecular Scale Eletronic Device Applications," J. Org. Chem., 61:6906-6921 (1996).

International Search Report in PCT/GB2004/004754 dated Mar. 11, 2005.

International Preliminary Report on Patentability for PCT/GB2004/004754, dated May 15, 2006.

Written Opinion of the International Searching Authority for PCT/GB2004/004754, dated Mar. 11, 2005.

Adrianus et al., "Lithium 2,2'-Biphenyldiyltrimethylsilicate; First Observation of Pentaorganosilicates," Angew. Chem. Int. Ed. Engl., 35(10):1127-1128 (1996).

Bacon et al., "Metal Ions and Complexes in Organic Reactions. Part XI. Reactions In Pyridine Between Copper Species and Aryl Halides, In Particular Between Copper (1) Oxide and 2-Bromonitrobenzene," J. Chem. Soc. (C), 1967-1973 (1970).

Ishikawa et al., "Chemistry of Siloles, The Reactions of Siloles With Organolithium Reagents," J. Organomet. Chem., 250:109-119 (1983).

Speight, Ph.D., Lange's Handbook of Chemistry, Sixteenth Edition, McGraw-Hill, pp. 2.703-2.706 (2005).

* cited by examiner

POLYMERS, THEIR PREPARATION AND USES

BACKGROUND OF THE INVENTION

1. Field of the Invention

The invention relates to polymers for electronic and optical applications and the synthesis thereof.

2. Related Technology

Organic semiconductors are attracting increasing attention across a wide range of applications due to their advantageous electronic properties and their processability. One class of opto-electrical devices is that using an organic material for light emission (an organic light-emissive device or "OLED") or for light absorption for the purpose of power generation or light detection (a photovoltaic device). The basic structure of these devices is a semiconducting organic layer, sandwiched between a cathode for injecting or accepting negative charge carriers (electrons) and an anode for injecting or accepting positive charge carriers (holes) into or from the organic layer. For example, an OLED is typically fabricated on a glass or plastic substrate coated with a transparent first electrode such as indium-tin-oxide ("ITO"). A layer of a thin film of at least one electroluminescent organic material covers the first electrode. Finally, a cathode covers the layer of electroluminescent organic material. The cathode is typically a metal or alloy and may comprise a single layer, such as aluminium, or a plurality of layers such as calcium and aluminium. Other layers can be added to the device, for example to improve charge injection from the electrodes to the electroluminescent material. For example, a hole injection layer such as poly (ethylene dioxythiophene)/polystyrene sulfonate (PEDOT-PSS) or polyaniline may be provided between the anode and the electroluminescent material. In a practical device one of the electrodes is transparent, to allow the photons to escape or enter the device.

In the case of an OLED, holes are injected into the highest occupied molecular orbital (HOMO) of the electroluminescent material and electrons are injected into its lowest unoccupied molecular orbital (LUMO). Holes and electrons then combine to generate excitons which undergo radiative decay, the wavelength of emission being at least partially dependant on the HOMO-LUMO bandgap. Organic materials for use as light-emissive materials include polymers such as poly(p-phenylenevinylene) (as disclosed in WO 90/13148), polyfluorenes and polyphenylenes; the class of materials known as small molecule materials such as tris-(8-hydroxyquinoline)aluminium ("Alq$_3$") as disclosed in U.S. Pat. No. 4,539,507; and the class of materials known as dendrimers as disclosed in WO 99/21935. These materials electroluminesce by radiative decay of singlet excitons (i.e. fluorescence) however spin statistics dictate that up to 75% of excitons are triplet excitons which undergo non-radiative decay, i.e. quantum efficiency may be as low as 25% for fluorescent OLEDs and so these materials or similar materials capable of transporting charge may be used as hosts for dopants comprising heavy metal complexes capable of harvesting triplet excitons for radiative decay (phosphorescence) as disclosed in, for example, *Pure Appl. Chem.*, 1999, 71, 2095, Materials Science & Engineering, R: Reports (2002), R39(5-6), 143-222 and Polymeric Materials Science and Engineering (2000), 83, 202-203.

Polyfluorenes having a repeat unit of formula (A) are disclosed in for example, Adv. Mater. 2000 12(23) 1737-1750:

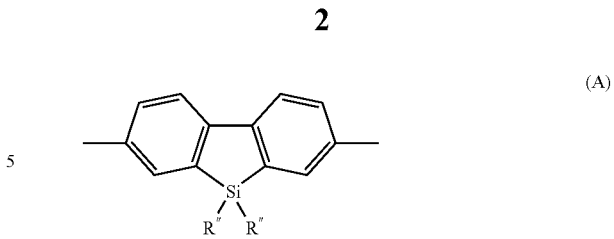

(A)

wherein R" represents a solubilizing group such as n-octyl.

These polymers have attracted considerable interest as electroluminescent materials because they are solution processable and have good film forming properties. Furthermore, these polymers may be made by Yamamoto or Suzuki polymerization, for which the appropriate monomers are accessed simply by halogenation of fluorene to form a 2,7-dihalofluorene. These polymerization techniques enable polymerization of fluorene monomers with a wide range of aromatic co-monomers and afford a high degree of control over regioregularity of the polymer. Thus, the physical and electronic properties of polyfluorenes may be tailored by appropriate selection of monomers.

Linkage of the fluorene repeat units through the 2- and 7-positions is important for maximization of conjugation through the repeat unit.

A focus in the field of PLEDs has been the development of full color displays for which red, green and blue electroluminescent polymers are required—see for example Synthetic Metals 111-112 (2000), 125-128. To this end, a large body of work has been reported in the development of electroluminescent polymers for each of these three colors with red, green and blue emission as defined by PAL standard 1931 CIE co-ordinates.

A difficulty encountered with blue electroluminescent polymers to date is that their lifetime (i.e. the time taken for brightness to halve from a given starting brightness at fixed current) tends to be shorter than that of corresponding red or green materials. One of the factors that has been proposed as contributing to the more rapid degradation of blue materials is that their LUMO levels, and consequently the energy level of the charged state following injection of an electron into the LUMO, tend to be less deep (i.e. relatively low electron affinity) than those of corresponding red or green materials. It is therefore possible that materials comprising these lower electron affinities are less electrochemically stable and so more prone to degradation.

For simplicity, a full color display will preferably have a common cathode material for all three electroluminescent materials. Thus, the problem of a large energy gap between the LUMO and the workfunction of the cathode for a typical blue electroluminescent material is likely to be exacerbated where a common cathode suitable for red and green materials is employed.

A blue electroluminescent material having a higher electron affinity than polyfluorenes or a material capable of injecting electrons into blue electroluminescent polymers is therefore desirable, however increasing the electron affinity of a wide bandgap material will tend to result in a smaller bandgap thus making the material less suitable as a blue emitter or as an electron transporting material for a blue emitter.

A further drawback of polyfluorenes is that blue electroluminescent polyfluorenes have a tendency to shift over time towards longer wavelengths, i.e. towards a redder colour of emission. This effect is believed to be due to oxidative degradation and aggregation of the polymer.

EP 1318163 discloses a monomer of formula (B), and electroluminescent polymers derived therefrom:

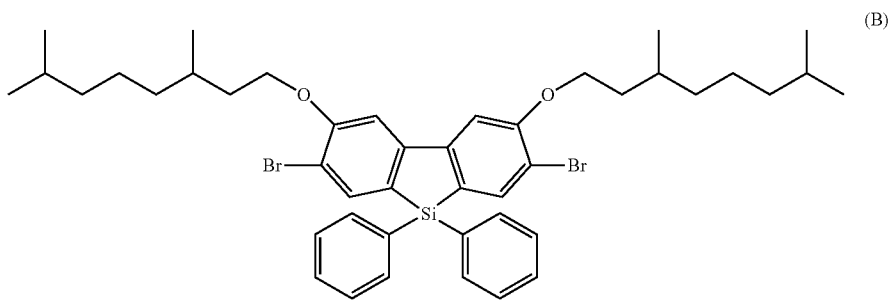 [SMILES: CC(C)CCCC(C)CCOc1cc2c(cc1Br)[Si](c1ccccc1)(c1ccccc1)c1cc(Br)c(OCCC(C)CCCC(C)C)cc1-2]
(B)

Likewise, JP 2003-206289 discloses a monomer of formula (C) and polymers derived therefrom:

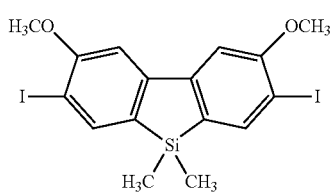
(C)

These disclosures teach formation of the above dibenzosilole monomers either via (a) lithiation of the 2- and 7-positions of the corresponding non-halogenated compound followed by halogen exchange, or (b) by the following process:

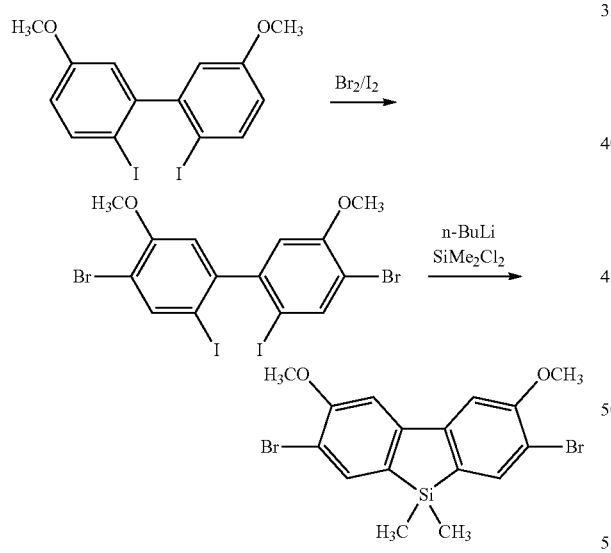

In case (a), the alkoxy groups serve to direct lithiation at the adjacent 2- and 7-positions. Likewise, in case (b) the alkoxy groups serve to direct bromination in the same way. Although these alkoxy groups are significant in monomer synthesis, they are likely to cause repeat units derived from such monomers to suffer from steric interference with adjacent repeat units resulting in a twist in the polymer backbone and loss of conductivity. Furthermore, the electron donating nature of these alkoxy groups decreases the electron affinity of polymers derived from these monomers.

A further drawback of polymers derived from monomers (B) and (C) is that the phenyl and methyl groups of these monomer do not afford solubility in common organic solvents such as xylene.

It is therefore an object of the invention to provide a wide bandgap polymer having higher electron affinity than a polyfluorene, i.e. a material capable of blue emission and capable of serving as an electron transporting material for other blue and smaller bandgap emissive materials. It is a further object of the invention to provide such a polymer that does not suffer from undesirable steric effects; that does not suffer from a color shift over time; and that is readily soluble in common organic solvents. It is a yet further object of the invention to provide a host material for luminescent dopants, in particular phosphorescent dopants.

SUMMARY OF THE INVENTION

The present inventors have found a novel class of dibenzosiloles that solve the aforementioned drawbacks of polyfluorenes.

Accordingly, in a first aspect the invention provides a polymer comprising an optionally substituted first repeat unit of formula (I):

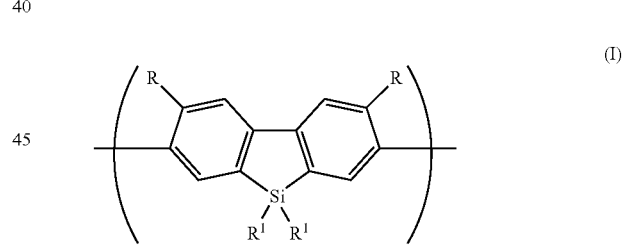
(I)

wherein each R is the same or different and represents H or an electron withdrawing group; and each $R^1$ is the same or different and represents a substituent.

Preferred electron withdrawing groups are selected from: groups comprising fluorine, cyano, nitro, carboxyl, amides, ketones, phosphinoyl, phosphonates, sulfones and esters. Preferred groups comprising fluorine include fluorine atoms, fluoroalkyl, fluoroaryl and fluoroheteroaryl.

Other electron withdrawing groups R will be apparent to the skilled person. In particular, those substituents having a positive Hammett sigma constant are suitable.

The present inventors have found that polymers according to the first aspect of the invention are high electron affinity, wide bandgap materials. In contrast to the prior art, polymers according to the invention do not possess electron-donating groups in the 3- and 6-positions that lessen the electron affinity of the dibenzosilole units.

In order to avoid steric interactions between adjacent repeat units, it is preferred that at least one R group is hydrogen. More preferably, both R groups are hydrogen.

Preferably, at least one $R^1$ is a solubilizing group.

Preferably, each $R^1$ is the same or different and is selected from the group consisting of optionally substituted $C_{1-20}$ alkyl, $C_{1-20}$ alkoxy, aryl and heteroaryl. More preferably, each $R^1$ is independently a $C_{4-10}$ alkyl, most preferably n-hexyl or n-octyl. The optional substituents, where present, are preferably electron withdrawing groups, in particular fluorine. One or more such substituents may be provided on each $R^1$ group.

Preferably, the polymer comprises an optionally substituted aryl or heteroaryl second repeat unit.

In a second aspect, the invention provides a monomer of formula (II):

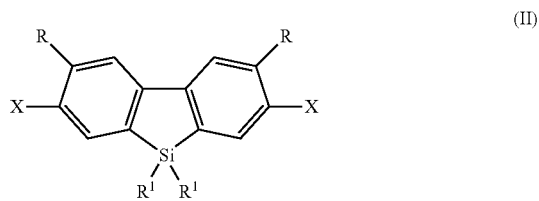

(II)

wherein R and $R^1$ are as described in the first aspect of the invention and each X is the same or different and represents a polymerisable group.

Preferably, each X is the same or different and is selected from the group consisting of boronic acid groups, boronic ester groups, borane groups and halide functional groups.

In a third aspect, the invention provides a method of forming a polymer comprising the step of polymerizing the monomer of formula (II).

Preferably, each X is independently selected from the group consisting of boronic acid groups, boronic ester groups and borane groups and halide functional groups and the polymerization is performed in the presence of a transition metal catalyst.

In one preferred embodiment of the third aspect, each X is the same or different and is a halide functional group, and the polymerization is performed in the presence of a nickel complex catalyst.

In another preferred embodiment of the third aspect, the method comprises polymerizing:

a monomer of formula (II) wherein each X is the same or different and is a boron derivative functional group selected from a boronic acid, a boronic ester and a borane, and an aromatic monomer having at least two reactive halide functional groups; or a monomer of formula (II) wherein each X is the same or different and is a reactive halide functional group, and an aromatic monomer having at least two boron derivative functional group selected from a boronic acid, a boronic ester and a borane; or a monomer of formula (II) wherein one X is a reactive halide functional group and the other X is a boron derivative functional group selected from a boronic acid, a boronic ester and a borane, wherein the reaction mixture comprises a catalytic amount of a palladium catalyst suitable for catalyzing the polymerization of the aromatic monomers, and a base in an amount sufficient to convert the boron derivative functional groups into boronate anionic groups.

In a fourth aspect, the invention provides an optical device comprising a polymer according to the first aspect of the invention.

Preferably, the optical device comprises an anode, a cathode and a layer of the polymer according to the first aspect of the invention located between the anode and the cathode.

Preferably, the optical device is an electroluminescent device.

In a fifth aspect, the invention provides a switching device comprising a polymer according to the first aspect of the invention.

Preferably, the switching device is a thin film transistor.

The present inventors have found that monomers of formula (II) may be formed from a class of key intermediates that do not require the presence of ortho-directing groups.

Accordingly, in a sixth aspect the invention provides an optionally substituted compound of formula (IV):

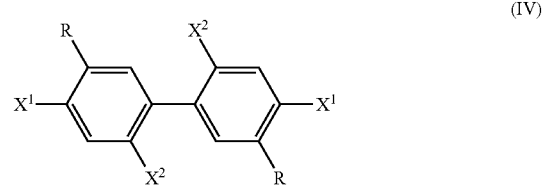

(IV)

wherein each $X^1$ and each $X^2$ is the same or different and represents a leaving group capable of participating in a transmetallation reaction and $X^2$ has an electronegativity less than that of $X^1$.

Preferably, both $X^1$ groups are the same and both $X^2$ groups are the same. Where the two groups $X^1$ and/or the two groups $X^2$ are different, it will be appreciated that the electronegativity of the least electronegative $X^1$ group shall be greater than the electronegativity of the most electronegative $X^2$ group.

Preferably, each $X^1$ and $X^2$ is independently a halogen. More preferably, $X^1$ and $X^2$ are selected from bromine, chlorine and iodine. Most preferably, $X^1$ is bromine and $X^2$ is iodine.

The compound of formula (IV) serves as an intermediate to a variety of monomers including but not limited to dibenzosiloles.

Accordingly, in a seventh aspect the invention provides a method of forming a monomer of formula (VI) from a compound of formula (V) according to the following scheme:

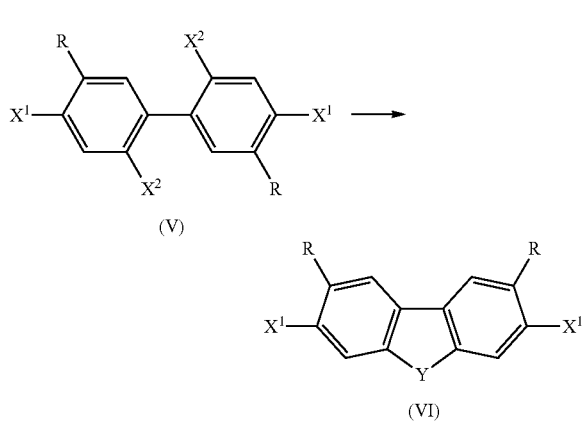

wherein the method comprises reacting the compound of formula (V) with a transmetallating agent followed by reaction with a compound of formula LG-Y-LG, wherein $X^1$ and R are as defined in the sixth aspect of the invention; each $X^3$ is the same or different and represents a leaving group capable of participating in a transmetallation having an electronegativity less than or the same as that of $X^1$; Y represents a divalent residue comprising a backbone of 1-3 atoms; and each LG is the same or different and represents a leaving group.

By "transmetallating agent" is meant a compound capable of reacting with the C—$X^2$ bond of the compound of formula (IV) to transform it into a carbon-metal bond.

Preferably, Y comprises a single atom in its backbone selected from the group consisting of —$CR^3{}_2$—, —$SiR^3{}_2$—, —$NR^3$—, —$PR^3$—, —$GeR^3{}_2$—, —$SnR^3{}_2$—, O and S, wherein $R^3$ is selected from the group consisting of optionally substituted alkyl, alkoxy, aryl and heteroaryl. More preferably, Y is selected from the group consisting of —$CR^3{}_2$—, —$SiR^3{}_2$—, —$NR^3$—, —$PR^3$—, —$GeR^3{}_2$—, —$SnR^3{}_2$—, O and S. Preferably, each $R^3$ is the same or different and is a $C_{1-20}$ alkyl.

Preferably, each LG is the same or different and is a halogen, more preferably chlorine, bromine or iodine.

Preferably, the transmetallating agent is a compound of formula $R^4$-M wherein $R^4$ is alkyl or aryl and M is a metal. Preferably, M is lithium. Preferably, $R^4$ is $C_{1-4}$ alkyl or phenyl.

As outlined above, linkage of dibenzosilole repeat units according to the invention through their 2- and 7-positions maximises conjugation of polymer chains comprising these repeat units. However, the present inventors have found that non-2,7-linked dibenzosiloles possess a wider bandgap than corresponding 2,7-linked dibenzosiloles and at the same time retain a desirable high electron affinity. Moreover, non-2,7-linked dibenzosiloles have been found to possess a higher triplet energy level than corresponding 2,7-linked dibenzosiloles and as such may serve as the host material for a wider range of fluorescent or phosphorescent dopants.

Accordingly, in an eighth aspect the invention provides a polymer comprising an optionally substituted first repeat unit of formula (VII):

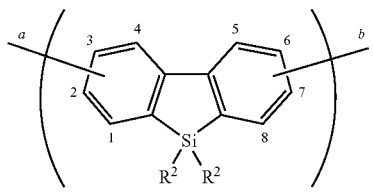

(VII)

wherein each $R^2$ is the same or different and represents a substituent; the $R^2$ groups may be linked to form a ring; and bond (a) is not linked to the 2-position of the repeat unit of formula (VII).

Bond (b) may or may not be bound to the 7-position of the repeat unit of formula (VII), however in a preferred embodiment bond (b) is not bound to the 7-position of the repeat unit of formula (VII).

Preferably, bond (a) is bound to the 3-position of the repeat unit of formula (VII).

Preferably, bond (b) is bound to the 6-position of the repeat unit of formula (VII).

Preferably, at least one $R^2$ is a solubilizing group.

Preferably, each $R^2$ is the same or different and is selected from the group consisting of optionally substituted $C_{1-20}$ alkyl, $C_{1-20}$ alkoxy, aryl and heteroaryl. More preferably, each $R^2$ is independently a $C_{4-10}$ alkyl, most preferably n-hexyl or n-octyl.

Preferably, the polymer comprises an optionally substituted aryl or heteroaryl second repeat unit.

In a ninth aspect the invention provides an optionally substituted monomer of formula (VIII):

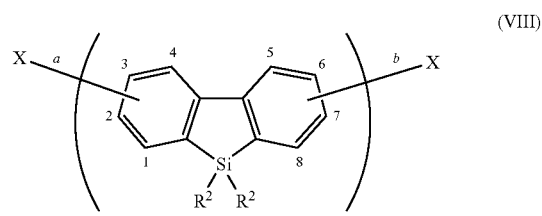

(VIII)

wherein each $R^2$ is as defined in the eighth aspect of the invention; each X is as defined in the second aspect of the invention and at least one X is not linked to the 2-position of the repeat unit of formula (VIII).

The monomer of formula (VIII) may be polymerised in accordance with the method described in the third aspect of the invention.

The present inventors have found that polymers comprising dibenzosilole repeat units function very effectively as host materials for luminescent dopants.

Accordingly, in a tenth aspect the invention provides an electroluminescent device comprising an anode, a cathode and an electroluminescent layer located between the anode and cathode wherein the electroluminescent layer comprises a polymeric host material comprising an optionally substituted first repeat unit of formula (IX) and a luminescent dopant

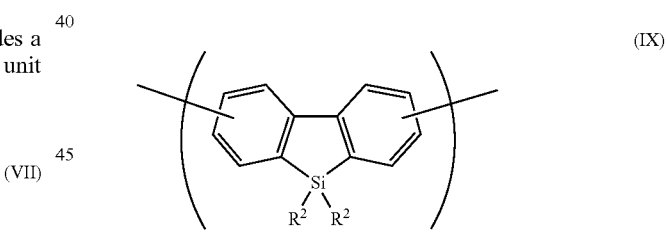

(IX)

wherein $R^1$ is as described in the first aspect of the invention.

Preferably, the repeat unit of formula (IX) is not linked through its 2-position. More preferably, the repeat unit of formula (IX) is not linked through its 2- or 7-positions. Most preferably, the repeat unit of formula (IX) is linked through its 3- and 6-positions.

Preferably, the polymer comprises a second repeat unit. Preferably, the second repeat unit comprises a hole transporting material. More preferably, the second repeat unit is a carbazole, more preferably a 3,6-linked carbazole.

The luminescent dopant may be phosphorescent or fluorescent. Preferably, the luminescent dopant is phosphorescent.

Preferably, the repeat unit of formula (IX) is unsubstituted.

Reaction of dibenzosiloles with organolithium reagents is disclosed in J. Organomet. Chem., 1983, 250, 109-119. In particular, transalkylation of 1-methyl-1-(trimethylsilyl)- and 1-methyl-1-(trimethylsilyl)-dibenzosilole with methyllithium, butyllithium and phenyllithium is disclosed. Angew. Chem. Int. Ed., 1996, 35, 1127-1128 indicates that such reactions proceed via a pentaco-ordinate intermediate.

The dibenzosiloles disclosed in this prior art do not carry any reactive groups other than at the silicon atom of the dibenzosilole where transalkylation takes place. The present inventors have surprisingly found that the substituents carried at the silicon atom of dibenzosiloles may selectively be changed, e.g. by transalkylation, even when reactive substituents are present elsewhere on the dibenzosilole.

Accordingly, in an eleventh aspect the invention provides a method of forming an optionally substituted compound of formula (X) according to the following process:

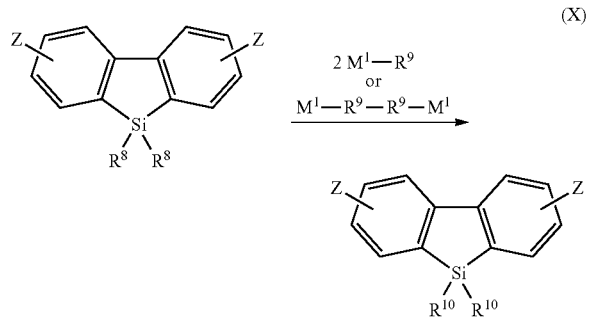

(X)

wherein each $R^8$ is independently selected from the group consisting of $C_{1-20}$ alkyl and aryl; each $R^9$ is different from $R^8$ and is independently selected from the group consisting of $C_{1-20}$ alkyl, aryl and heteroaryl; $M^1$ is a metal; and Z is a reactive group capable of undergoing reaction with $M^1$-$R^9$.

Preferably, $M^1$ is lithium.

Preferably, $R^8$ is methyl.

Preferably, Z is trialkylsilyl, more preferably trimethylsilyl.

In case of reaction with $M^1$-$R^9$ the two groups $R^{10}$ are not linked to form a ring. Preferred groups $R^9$ in this case are $C_{4-20}$ alkyl.

In case of reaction with $M^1$-$R^9$—$R^9$-$M^1$ the two groups $R^{10}$ are linked to form a ring. In this case, preferred groups $R^9$—$R^9$ are $C_{4-20}$ alkylene or optionally substituted biaryl or bi-heteroaryl, in particular biphenyl.

A particularly preferred compound of formula $M^1$-$R^9$—$R^9$-$M^1$ has the structure shown below, which may optionally be substituted:

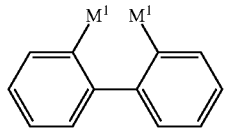

BRIEF DESCRIPTION OF THE DRAWINGS

The present invention will now be described in further detail, by way of example only, with reference to the accompanying drawings in which.

DETAILED DESCRIPTION OF THE INVENTION

Figure 1:
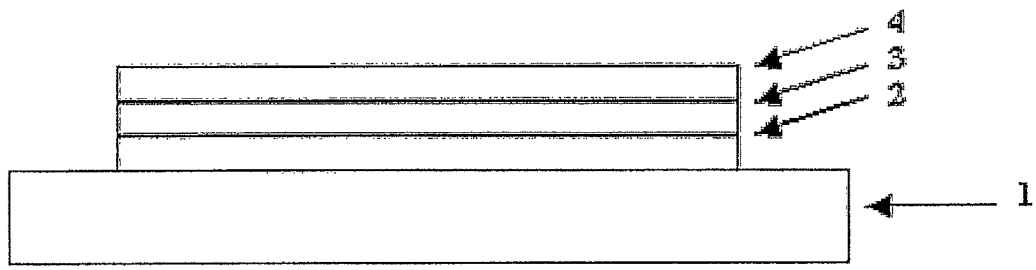
FIG. 1 shows a prior art electroluminescent device

A polymer according to the present invention may comprise a homopolymer or copolymers (including terpolymers or higher order polymers).

Copolymers according to the present invention include regular alternating, random and block polymers where the percentage of each monomer used to prepare the polymer may vary.

Preferred co-repeat units include triarylamines, arylenes and heteroarylenes.

Examples of arylene repeat units are fluorene, particularly 2,7-linked 9,9 dialkyl fluorene or 2,7-linked 9,9 diaryl fluorene; spirofluorene such as 2,7-linked 9,9-spirofluorene; indenofluorene such as a 2,7-linked indenofluorene; or phenyl such as alkyl or alkoxy substituted 1,4-phenylene. Each of these groups may optionally be substituted.

Particularly preferred triarylamine repeat units derived from triarylamine monomers include units of formulae 1-6:

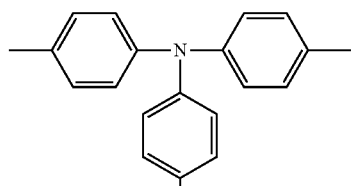

1

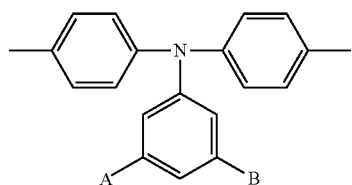

2

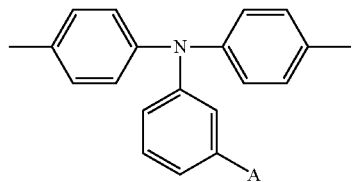

3

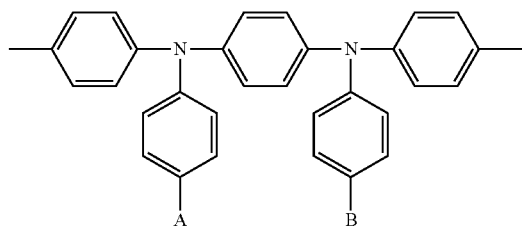

4

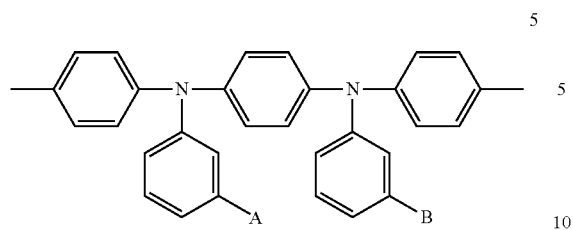
5

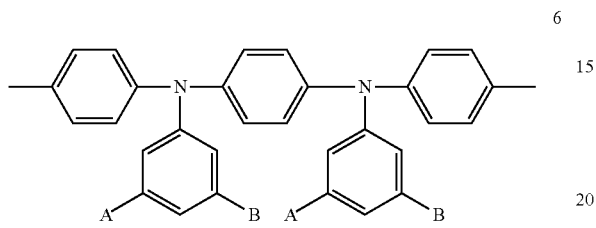
6

A and B may be the same or different and are substituent groups. It is preferred that one or both of A and B is independently selected from the group consisting of alkyl, aryl, perfluoroalkyl, thioalkyl, cyano, alkoxy, heteroaryl, alkylaryl and arylalkyl groups. One or more of A and B also may be hydrogen. It is preferred that one or more of A and B is independently an unsubstituted, isobutyl group, an n-alkyl, an n-alkoxy or a trifluoromethyl group because they are suitable for helping to select the HOMO level and/or for improving solubility of the polymer.

Particularly preferred heteroaryl repeat units include units of formulae 7-21:

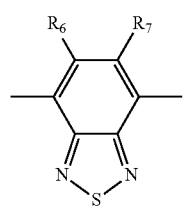
7 wherein $R_6$ and $R_7$ are the same or different and are each independently hydrogen or a substituent group, preferably alkyl, aryl, perfluoroalkyl, thioalkyl, cyano, alkoxy, heteroaryl, alkylaryl or arylalkyl. For ease of manufacture, $R_6$ and $R_7$ are preferably the same. More preferably, they are the same and are each a phenyl group.

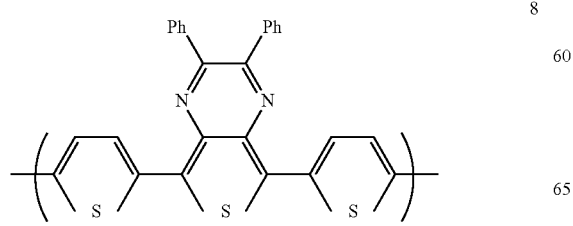
8

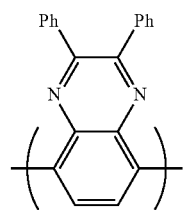
9

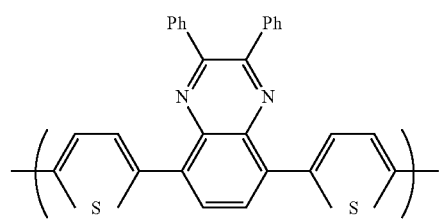
10

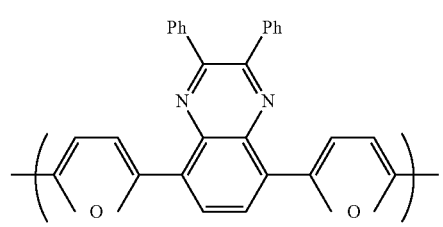
11

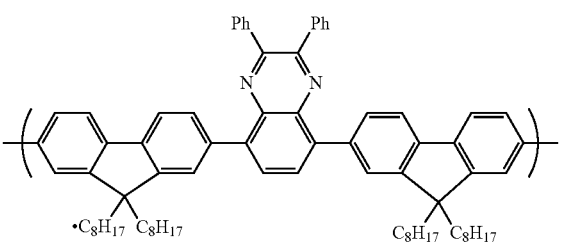
12

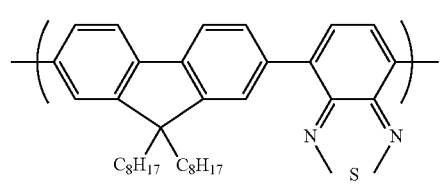
13

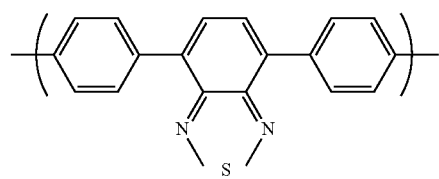
14

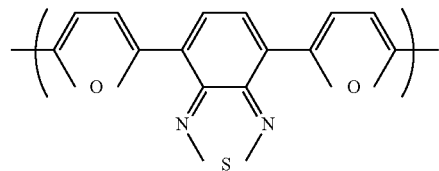
15

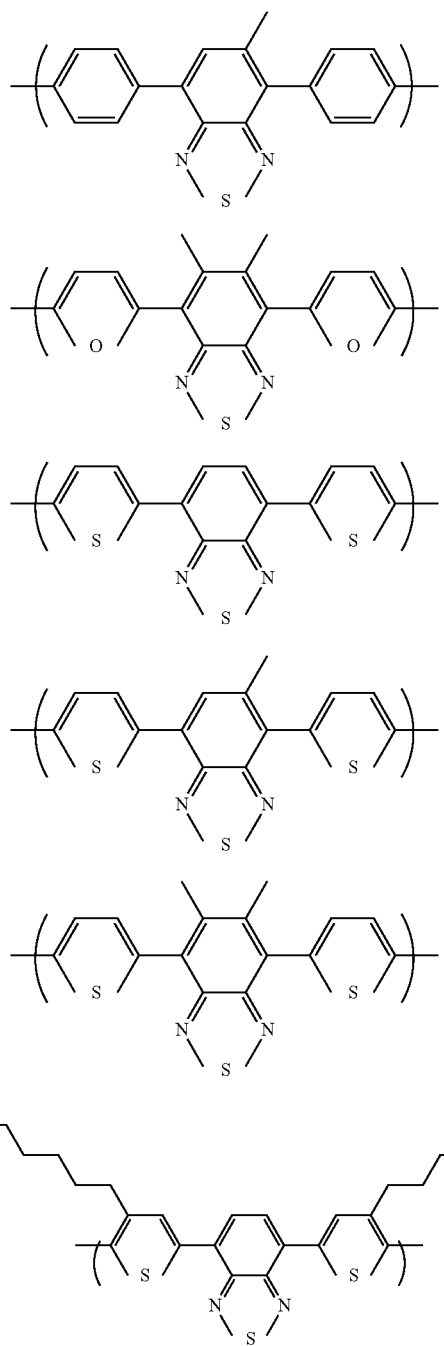

Further suitable Ar groups are known in this art, for example as disclosed in WO 00/55927 and WO 00/46321, the contents of which are incorporated herein by reference.

For ease of processing, it is preferred that the polymer is soluble. Substituents such as $C_{1-10}$ alkyl or $C_{1-10}$ alkoxy may usefully be selected to confer on the polymer solubility in a particular solvent system. Typical solvents include mono- or poly-alkylated benzenes such as toluene and xylene or tetrahydrofuran. Techniques for solution deposition of the polymer according to the invention include inkjet printing as disclosed in EP 0880303, spin-coating, dip-coating, doctor blade coating and screen printing.

The polymers according to the invention may carry cross-linkable groups such as oxetanes, azides, acrylates, vinyl and ethynyl groups in order that the polymer may be deposited in a soluble form followed by cross-linking to render the polymer insoluble. Cross-linking may be achieved through thermal treatment or exposure of the polymer to radiation, in particular UV radiation. Cross-linking may be employed to allow deposition of multiple layers from solution as disclosed in WO 96/20253. Alternatively, photo-initiated cross-linking may be used by exposure of a polymer layer through a mask to form a pattern of insoluble material from which unexposed, soluble polymer may be removed by solvent treatment as disclosed in Nature 421, 829-833, 2003.

Two polymerisation techniques that are particularly amenable to preparation of conjugated polymers from aromatic monomers such as dibenzosilole monomers according to the invention are Suzuki polymerisation as disclosed in, for example, WO 00/53656 and Yamamoto polymerisation as disclosed in, for example, "Macromolecules", 31, 1099-1103 (1998). Suzuki polymerisation entails the coupling of halide and boron derivative functional groups; Yamamoto polymerisation entails the coupling of halide functional groups. Accordingly, it is preferred that each monomer is provided with two reactive functional groups wherein each functional group is independently selected from the group consisting of (a) boron derivative functional groups selected from boronic acid groups, boronic ester groups and borane groups and (b) halide functional groups.

The transmetallating agents used to prepare monomers of the invention include alkyl- and aryl-lithium compounds such as methyllithium, n-butyllithium, t-butyllithium, phenyl-lithium and lithium di-isopropyl amine.

Examples of monomers of formula (VI) preparable according to the method of the invention include the following:

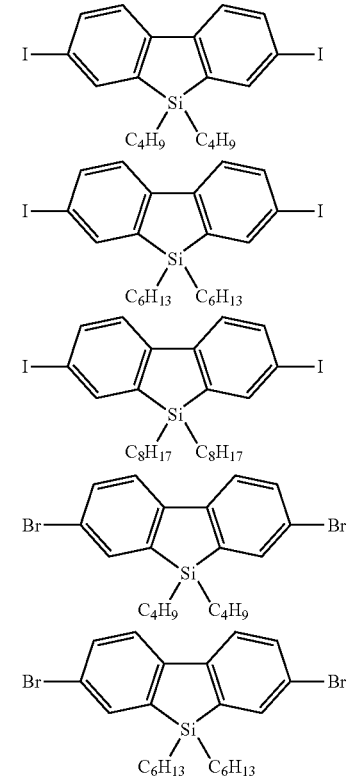

-continued

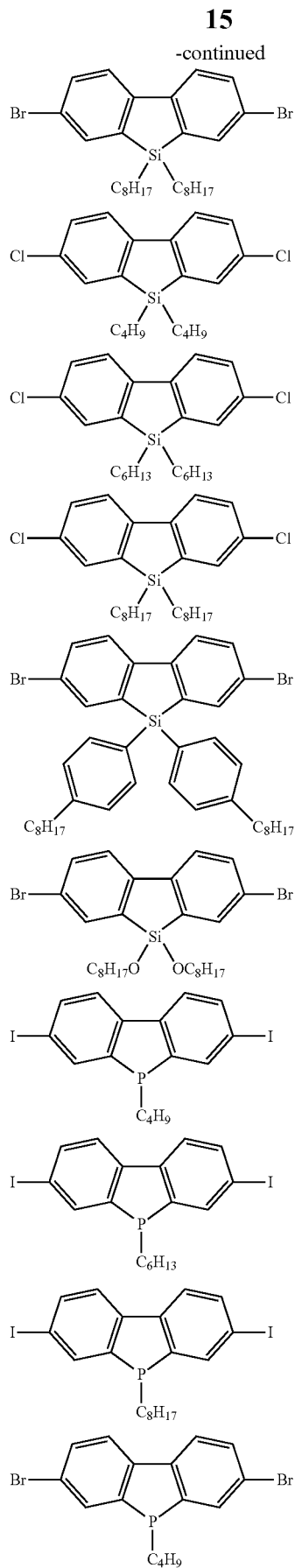

-continued

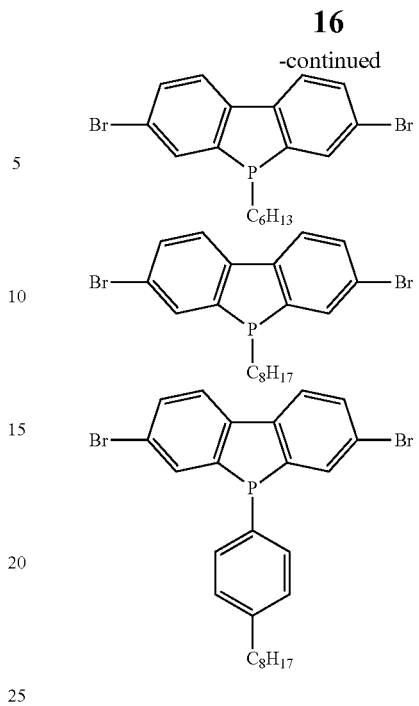

With reference to FIG. 1, the standard architecture of an optical device according to the invention, in particular an electroluminescent device, comprises a transparent glass or plastic substrate 1, an anode of indium tin oxide 2 and a cathode 4. The polymer according to the invention is located in layer 3 between anode 2 and cathode 4. Layer 3 may comprise the polymer according to the invention alone or a plurality of polymers. Where a plurality of polymers are deposited, they may comprise a blend of at least two of a hole transporting polymer, an electron transporting polymer and, where the device is a PLED, an emissive polymer as disclosed in WO 99/48160. Alternatively, layer 3 may be formed from a single polymer that comprises regions selected from two or more of hole transporting regions, electron transporting regions and emissive regions as disclosed in, for example, WO 00/55927 and U.S. Pat. No. 6,353,083. Each of the functions of hole transport, electron transport and emission may be provided by separate polymers or separate regions of a single polymer. Alternatively, more than one function may be performed by a single region or polymer. In particular, a single polymer or region may be capable of both charge transport and emission. Each region may comprise a single repeat unit, e.g. a triarylamine repeat unit may be a hole transporting region. Alternatively, each region may be a chain of repeat units, such as a chain of polyfluorene or dibenzosilole units as an electron transporting region. The different regions within such a polymer may be provided along the polymer backbone, as per U.S. Pat. No. 6,353,083, or as groups pendant from the polymer backbone as per WO 01/62869.

In addition to layer 3, a separate hole transporting layer and/or an electron transporting layer may be provided.

The polymers according to the invention may be used as the host for a fluorescent dopant as disclosed in, for example, J. Appl. Phys. 65, 3610, 1989 or as the host for a phosphorescent dopant as disclosed in, for example, Nature (London), 1998, 395, 151.

Preferred metal complexes comprise optionally substituted complexes of formula (XI):

$$M^1L^1{}_qL^2{}_rL^3{}_s \qquad (XI)$$

wherein $M^1$ is a metal; each of $L^1$, $L^2$ and $L^3$ is a coordinating group; q is an integer; r and s are each independently 0 or an integer; and the sum of (a. q)+(b. r)+(c.s) is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet states (phosphorescence). Suitable heavy metals M include:

lanthanide metals such as cerium, samarium, europium, terbium, dysprosium, thulium, erbium and neodymium; and d-block metals, in particular those in rows 2 and 3 i.e. elements 39 to 48 and 72 to 80, in particular ruthenium, rhodium, palladium, rhenium, osmium, iridium, platinum and gold.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure color emission useful for display applications.

The d-block metals form organometallic complexes with carbon or nitrogen donors such as porphyrin or bidentate ligands of formula (XII):

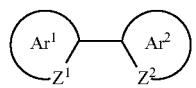

(XII)

wherein $Ar^1$ and $Ar^2$ may be the same or different and are independently selected from optionally substituted aryl or heteroaryl; $Z^1$ and $Z^2$ may be the same or different and are independently selected from carbon or nitrogen; and $Ar^1$ and $Ar^2$ may be fused together. Ligands wherein $Z^1$ is carbon and $Z^2$ is nitrogen are particularly preferred.

Examples of bidentate ligands are illustrated below:

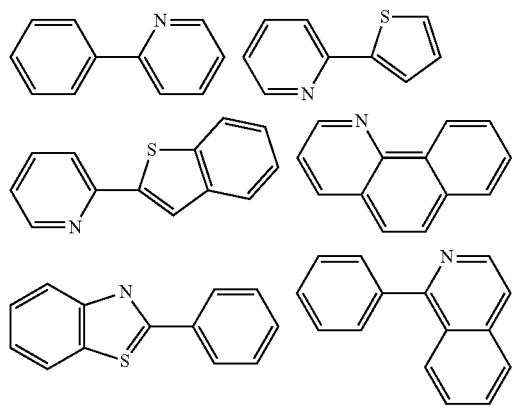

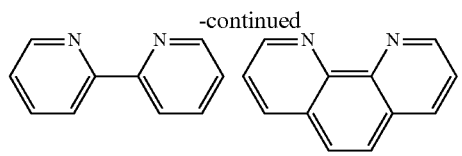

-continued

Each of $Ar^1$ and $Ar^2$ may carry one or more substituents. Particularly preferred substituents include fluorine or trifluoromethyl which may be used to blue-shift the emission of the complex as disclosed in WO 02/45466, WO 02/44189, US 2002-117662 and US 2002-182441; alkyl or alkoxy groups as disclosed in JP 2002-324679; carbazole which may be used to assist hole transport to the complex when used as an emissive material as disclosed in WO 02/81448; bromine, chlorine or iodine which can serve to functionalise the ligand for attachment of further groups as disclosed in WO 02/68435 and EP 1245659; and dendrons which may be used to obtain or enhance solution processability of the metal complex as disclosed in WO 02/66552.

Other ligands suitable for use with d-block elements include diketonates, in particular acetylacetonate (acac); triarylphosphines and pyridine, each of which may be substituted.

Main group metal complexes show ligand based, or charge transfer emission. For these complexes, the emission color is determined by the choice of ligand as well as the metal. A wide range of fluorescent low molecular weight metal complexes are known and have been demonstrated in organic light emitting devices [see, e.g., Macromol. Sym. 125 (1997) 1-48, U.S. Pat. Nos. 5,150,006, 6,083,634 and 5,432,014], in particular tris-(8-hydroxyquinoline)aluminium. Suitable ligands for di or trivalent metals include: oxinoids, e.g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate and hydroxyquinoxalinol-10-hydroxybenzo (h) quinolinato (II), benzazoles (III), Schiff bases, azoindoles, chromone derivatives, 3-hydroxyflavone, and carboxylic acids such as salicylato amino carboxylates and ester carboxylates. Optional substituents include halogen, alkyl, alkoxy, haloalkyl, cyano, amino, amido, sulfonyl, carbonyl, aryl or heteroaryl on the (hetero) aromatic rings which may modify the emission color.

The metal complex may be incorporated into the host polymer of the invention, either as a substituent on the main chain of the polymer or incorporated into the main chain of the polymer, as disclosed in, for example, EP 1245659, WO 02/31896, WO 03/18653 and WO 03/22908. In this case, the polymer may provide the functions of emission and at least one of hole transport and electron transport.

The host polymer of the invention may be a homopolymer or a copolymer. In the case of copolymers, suitable co-repeat units include carbazoles, such as 2,7-linked carbazole repeat units. Alternatively, 3,6-linked carbazole repeat units as disclosed in J. Am. Chem. Soc. 2004, 126, 6035-6042 may also be used.

It is reported in J. Am. Chem. Soc. 2004, 126, 6035-6042 that shorter poly paraphenylene chains within the host backbone increases the triplet energy level of the host. It will therefore be appreciated that a higher triplet energy level for copolymers comprising a repeat unit according to the invention is achieved using a 3,6-linked carbazole repeat unit and a 3,6-linked dibenzosilole repeat unit according to the eighth aspect of the invention, as compared to a copolymer with units linked through 2,7-positions. Similarly, see "Carbazole Compounds as Host Materials for Triplet Emitters in Organic Light Emitting Diodes: Polymer Hosts for High Efficiency Light Emitting Diodes" Addy van Dijken, Jolanda J. A. M. Bastiaansen, Nicole M. M. Kiggen, Bea M. W. Langeveld, Carsten Rothe, Andy Monkman, Ingrid Bach, Philipp Stössel, and Klemens Brunner, J. Am. Chem. Soc. ASAP Articles, Web Release Date: 28 May 2004. Accordingly, a preferred host material has formula (XIII)

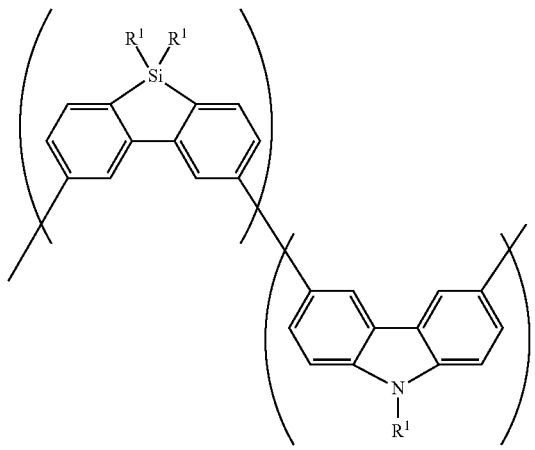

(XIII)

wherein $R^1$ is as defined in the first aspect of the invention. Polymers of this type may comprise blocks of the illustrated dibenzosilole and carbazole units, however in a particularly preferred embodiment the polymer (XIII) is a 1:1 copolymer of alternating dibenzosilole and carbazole units.

Other suitable co-repeat units for host co-polymers according to the invention include triarylamine repeat units of formulae 1-6 described above. Accordingly, another preferred host polymer has formula (XIV):

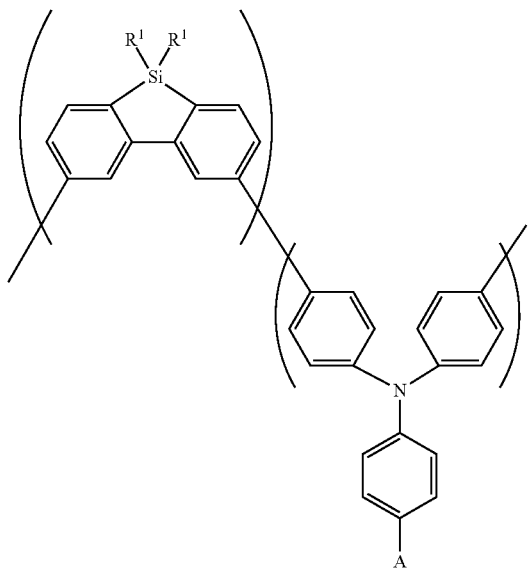

(XIV)

wherein $R^1$ is as defined in the first aspect of the invention and A is as defined above. Polymers of this type may comprise blocks of the illustrated dibenzosilole and triarylamine units, however in a particularly preferred embodiment the polymer (XIV) is a 1:1 copolymer of alternating dibenzosilole and carbazole units.

Although not essential, a layer of organic hole injection material (not shown) between the anode 2 and the polymer layer 3 is desirable because it assists hole injection from the anode into the layer or layers of semiconducting polymer. Examples of organic hole injection materials include poly (ethylene dioxythiophene) (PEDT/PSS) as disclosed in EP 0901176 and EP 0947123, or polyaniline as disclosed in U.S. Pat. Nos. 5,723,873 and 5,798,170.

Cathode 4 is selected from materials that have a workfunction allowing injection of electrons into the electroluminescent layer. Other factors influence the selection of the cathode such as the possibility of the adverse interactions between the cathode and the electroluminescent material. The cathode may consist of a single material such as a layer of aluminium. Alternatively, it may comprise a plurality of metals, for example a bilayer of calcium and aluminium as disclosed in WO 98/10621, elemental barium disclosed in WO 98/57381, Appl. Phys. Lett. 2002, 81(4), 634 and WO 02/84759 or a thin layer of dielectric material to assist electron injection, for example lithium fluoride disclosed in WO 00/48258 or barium fluoride, disclosed in Appl. Phys. Lett. 2001, 79(5), 2001.

A typical electroluminescent device comprises an anode having a workfunction of 4.8 eV. Accordingly, the HOMO level of the hole transporting region is preferably around 4.8-5.5 eV. Similarly, the cathode of a typical device will have a workfunction of around 3 eV. Accordingly, the LUMO level of the electron transporting region is preferably around 3-3.5 eV.

The polymers according to the invention may also be used in current switching devices for an integrated circuit as disclosed in, for example, WO 99/54936. In particular, the polymer may be a component of a field effect transistor comprising an insulator with a gate electrode located on one side of the insulator; a polymer according to the invention located on the other side of the insulator; and a drain electrode and a source electrode located on the polymer.

Electroluminescent devices may be monochrome devices or full colour devices (i.e. formed from red, green and blue electroluminescent materials).

EXAMPLES

A) 2,7-linked dibenzosilole monomers and repeat units

Monomer Example

Monomers 1 and 2 according to the second aspect of the invention was synthesised according to the following reaction scheme.

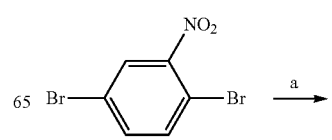

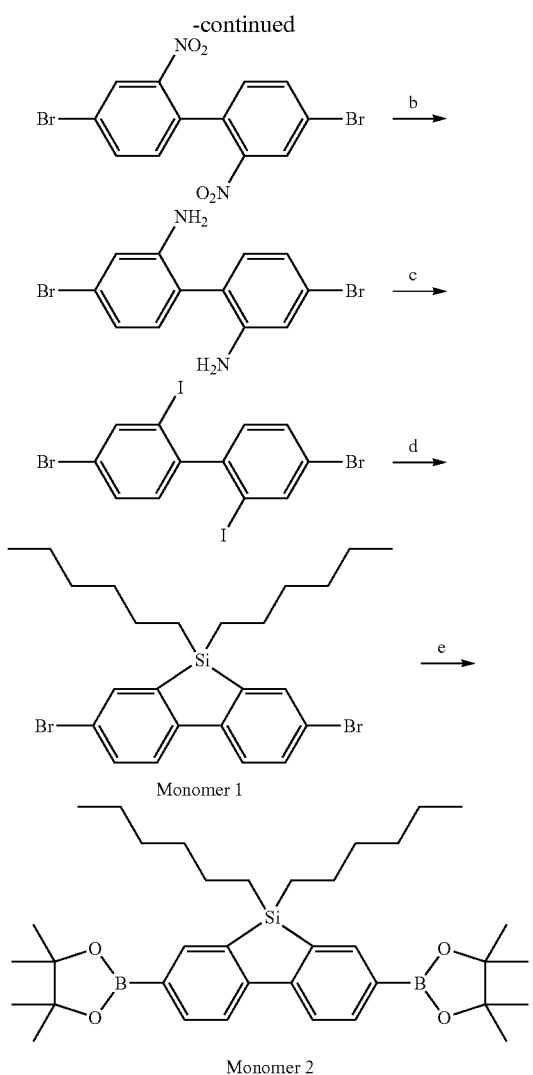

Monomer 1

Monomer 2 a) Cu, DMF, 125° C., 3 h, 75%; b) Sn, HCl, EtOH, 110° C., 2 h, 72%; c) (i) NaNO$_2$, HCl, 0° C., 1 h (ii) KI, −10 to 50° C., 2 h, 15%; d) (i) t-BuLi, THF, −90 to −78° C., 2 h (ii) Si(n-hexyl)$_2$Cl$_2$, 24 h, 52%; e) (i) t-BuLi, diethyl ether, −78° C., 1 h (ii) 2-isopropoxy-4,4',5,5'-tetramethyl-1,3,2-dioxaboralane, room temperature, 24 h, 74%.

4,4'-Dibromo-2,2'-dinitro-biphenyl

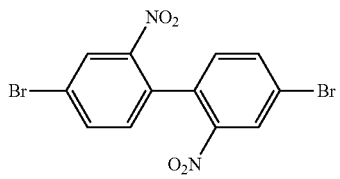

Reference: R. G. R. Bacon and S. G. Pande, *J. Chem. Soc.*, 1970, 1967.

To a solution of 2,5-dibromonitrobenzene (50.0 g, 179 mmol) in DMF (200 cm$^3$) was added copper powder (27.0 g, 424 mmol) and the reaction mixture heated to 125° C. After 3 h, the mixture was allowed to cool to room temperature and then treated with toluene (200 cm$^3$). The insoluble inorganic salts were removed by filtration through celite and the filtrate was evaporated to dryness. The crude material was vigorously washed with methanol (500 cm$^3$) and redissolved in toluene (200 cm$^3$). The remaining inorganic salts were again removed by filtration through celite, and the filtrate was evaporated to yield the title compound (27.1 g, 75%) as yellow crystals (Found: C, 35.8; H, 1.5; N, 6.7. C$_{12}$H$_6$Br$_2$N$_2$O$_4$ requires C, 35.9; H, 1.5; N, 7.0%); $v_{max}$/cm$^{-1}$ (Neat solid) 730, 829, 1004, 1103, 1344, 1526; $\delta_H$(500 MHz, CDCl$_3$) 7.18 (2H, d, J 8.2, ArH), 7.85 (2H, dd, J 8.2, 2.0, ArH), 8.39 (2H, d, J 2.0, ArH); $\delta_C$(100 MHz, CDCl$_3$) 122.9, 128.1, 131.9, 132.0, 136.6, 147.4.

4,4'-Dibromo-biphenyl-2,2'-diamine

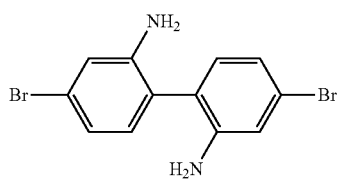

Reference: Patrick, D. A.; Boykin, D. W.; Wilson, W. D.; Tanious, F. A.; Spychala, J.; Bender, B. C.; Hall, J. E.; Dykstra, C. C.; Ohemeng, K. A.; Tidwell, R. R., *Eur. J. Med. Chem.*, 1997, 32(10), 781.

To a solution of 4,4'-Dibromo-2,2'-dinitro-biphenyl (15.0 g, 37.3 mmol) in ethanol (abs., 186 cm$^3$) was added 32% w/w aqueous HCl (124 cm$^3$). Tin powder (17.6 g, 147 mmol) was added portion-wise over 10 minutes and the reaction mixture was heated to reflux at 100° C. for 2 hours. After cooling, the mixture was poured into ice water (ca. 400 cm$^3$) and then basified with 20% w/w aqueous NaOH solution (150 cm$^3$). The product was extracted with diethyl ether and the organic layer washed with brine, dried over anhydrous MgSO$_4$ and evaporated to dryness. Purification by recrystallization from ethanol afforded the title compound (9.2 g, 72%) as light brown crystals (Found: C, 42.1; H, 3.0; N, 8.0. C$_{12}$H$_{10}$Br$_2$N$_2$ requires C, 42.2; H, 3.0; N 8.2%); $v_{max}$/cm$^{-1}$ (Neat solid) 792, 994, 1406, 1477, 1608, 3210, 3357, 3443; $\delta_H$(400 MHz, CDCl$_3$) 6.92 (6H, s, ArH), 3.78 (4H, brs, NH$_2$); $\delta_C$(100 MHz, CDCl$_3$) 118.1, 121.7, 122.0, 122.7, 132.2, 145.4; m/z (ES) 340.9283 ([M+H]$^+$. C$_{12}$H$_{11}$Br$_2$N$_2$ requires 340.9284), 343.1 (100%), 263.1 (80), 185.1 (25).

4,4'-Dibromo-2,2'-diiodo-biphenyl

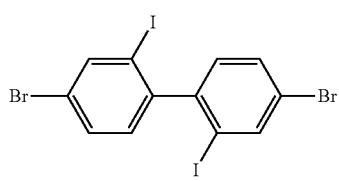 [SMILES: Brc1ccc(-c2ccc(Br)cc2I)c(I)c1]

4,4'-Dibromo-biphenyl-2,2'-diamine (5.0 g, 14.6 mmol) was suspended in 16% w/w aqueous. HCl (16 cm$^3$) at 0° C. Sodium nitrite (2.2 g, 31.9 mmol) was added dropwise whilst maintaining the temperature at 0° C. After a further 60 minutes of stirring at 0° C., KI solution (5.0 g, 30.1 mmol in 5 cm$^3$ H$_2$O) was added dropwise to the reaction mixture at −10° C.

The reaction mixture was allowed to warm to room temperature, and then to 50° C. for 2 h. The crude reaction mixture was allowed to cool to room temperature and then basified with 10% w/w aqueous NaOH (90 cm³). The product was extracted into diethyl ether and the organic layer washed with brine, dried with anhydrous MgSO₄ and evaporated. Purification by column chromatography (hexane) yielded the title compound (1.45 g, 15%) as an off-white solid (Found: C, 25.8; H, 1.0. $C_{12}H_6Br_2I_2$ requires C, 25.6; H, 1.1%); mp 89° C.; $v_{max}/cm^{-1}$ (Neat solid) 710, 817, 993, 1086, 1448, 1565; $\delta_H$(400 MHz, CDCl₃) 7.03 (2H, d, J 8.2, ArH), 7.55 (2H, dd, J 8.2 1.9, ArH), 8.08 (2H, d, J 1.9, ArH); $\delta_C$(100 MHz, CDCl₃) 99.8, 122.5, 130.7, 131.4, 141.0, 146.8.

2,7-Dibromo-9,9'-dihexyl-9H-9-dibenzosiloledibenzosilole

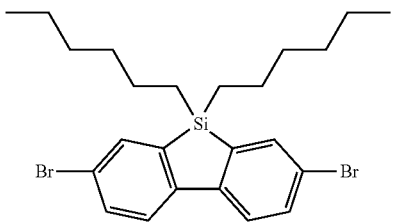 [SMILES: CCCCCC[Si]1(CCCCCC)c2cc(Br)ccc2-c2ccc(Br)cc21]

t-Butyllithium (6.26 cm³, 10.6 mmol, 1.7 M in Pentane) was added over 2 h to a solution of 4,4'-dibromo-2,2'-diiodobiphenyl (1.5 g, 2.66 mmol) in dry THF (30 cm³) at −90° C. under nitrogen atmosphere. The mixture was stirred for a further 1 h at −90° C. Dichlorodihexylsilane was subsequently added and the mixture was stirred at room temperature overnight. The reaction was quenched with distilled water, and the THF was removed by vacuum. The product was then extracted into diethyl ether and the organic layer washed with brine, dried with anhydrous MgSO₄ and evaporated. Purification by column chromatography (hexane) yielded the title compound (0.7 g, 52%) as a colorless oil; $v_{max}/cm^{-1}$ (Neat liquid) 720, 813, 1001, 1072, 1384, 2855, 2923, 2956; $\delta_H$(500 MHz, CDCl₃) 0.84-0.97 (10H, m, CH₂+CH₃), 1.22-1.36 (16H, m, CH₂), 7.55 (2H, dd, J 8.3 2.0, ArH), 7.64 (2H, d, J 8.3, ArH), 7.70 (2H, d, J 2.0, ArH); $\delta_C$(100 MHz, CDCl₃) 12.0, 14.0, 22.5, 23.7, 31.3, 32.9, 122.2, 122.5, 133.0, 140.4, 146.0; $\delta_{Si}$(100 MHz, CDCl₃) 4.1.

2,7-bis(4,4,5,5-tetramethyl-1,3,2-dioxaborolane-2-yl)-9,9-dihexyl-9H-9-dibenzosiloledibenzosilole

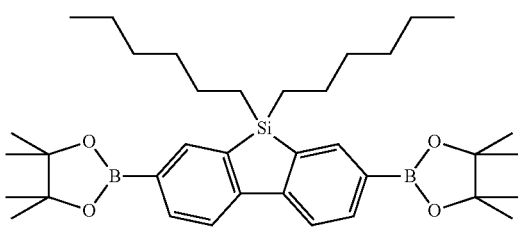

t-Butyllithium (1.19 cm³, 2.02 mmol, 1.7 M in Pentane) was added over 30 minutes to a solution of 2,7-dibromo-9,9'-dihexyl-9H-9-dibenzosilole (0.25 g, 0.49 mmol) in dry THF (3 cm³) at −78° C. under nitrogen atmosphere. The mixture was stirred for a further 1 h at −78° C. 2-Isopropoxy-4,4',5,5'-tetramethyl-1,3,2-dioxaboralane (0.25 cm³, 2.02 mmol) was then added dropwise to the mixture and stirring continued overnight at room temperature. The reaction was quenched with distilled water, and the THF was removed by vacuum. The product was then extracted into diethyl ether and the organic layer washed with brine, dried with anhydrous MgSO₄ and evaporated. Purification by column chromatography (hexane) using florisil yielded the title compound (0.22 g, 74%) as a white solid (Found: C, 71.2; H, 9.5. $C_{36}H_{56}Br_2O_4Si$ requires C, 71.8; H, 9.4%); $v_{max}/cm^{-1}$ (Neat liquid) 1093, 1143, 1345, 1597, 2922; $\delta_C$(100 MHz, CDCl₃) 12.3, 14.1, 22.6, 23.8, 24.9, 31.3, 33.0, 83.7, 120.5, 136.8, 137.5, 139.7, 151.0; $\delta_{Si}$(100 MHz, CDCl₃) 3.2.

Monomers according to the second aspect of the invention may alternatively be prepared according to the process set out below wherein the intermediate compound 2,2'-dibromo-4,4'-di(trimethylsilyl)-1,1'-biphenyl is firstly prepared according to the reaction scheme shown below:

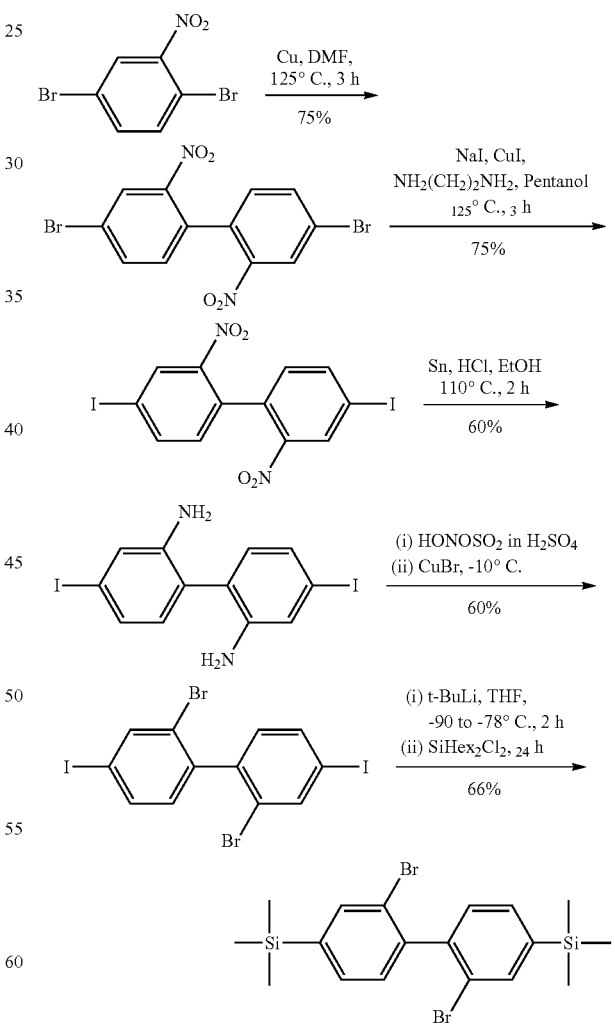

The monomer according to the second aspect of the invention may be derived from this biphenyl intermediate by one of two routes:

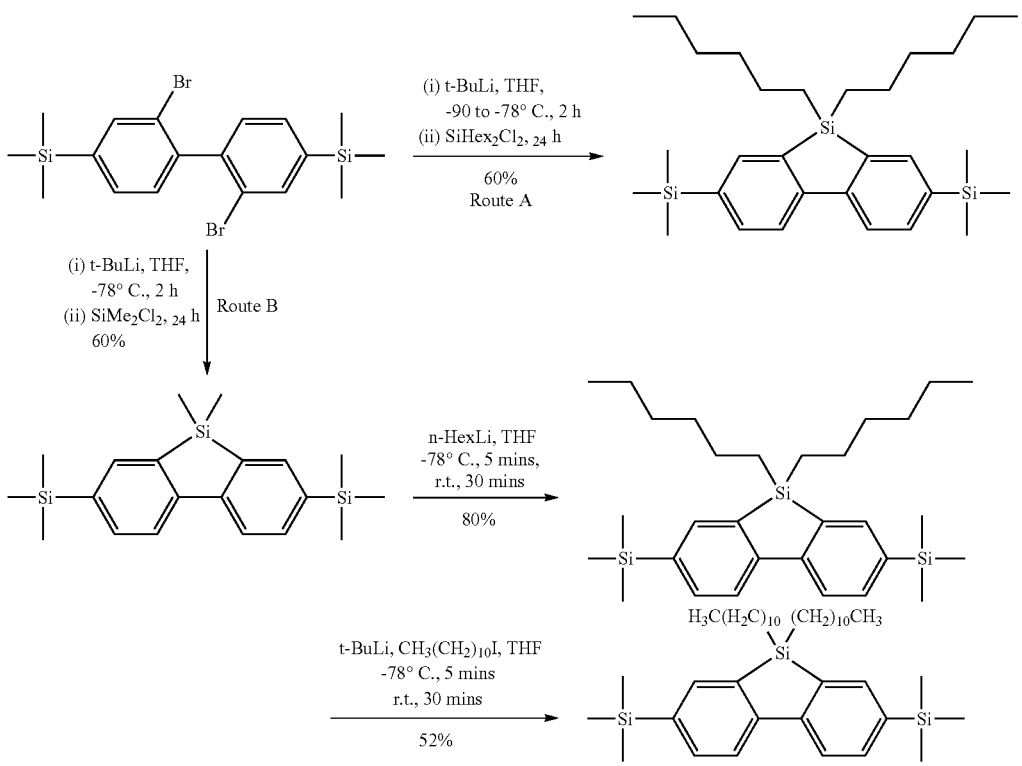

Surprisingly, it is possible to perform selective transalkylation of the dimethylsilyl group obtained through Route B above without affecting the trimethylsilyl end groups.

This allows for a wide number of substituents to be formed on the silicon atom, for example hexyl and undecyl as illustrated in the above scheme.

Polymer Examples

Polymer Example 1

A homopolymer according to the first aspect of the invention was prepared by Suzuki polymerization of Monomer 1 and Monomer 2 followed by end-capping with bromobenzene and phenylboronic acid according to the following scheme to afford dibenzosilole polymer PS6:

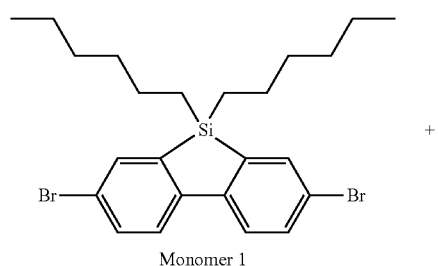

Monomer 1

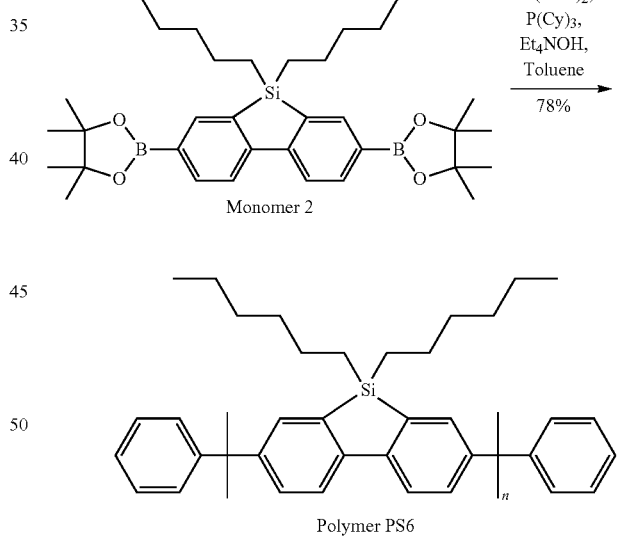

To a dried Schlenk tube was added 2,7-dibromo-9,9-dihexyl-9H-9-dibenzosilole (84 mg, 0.17 mmol, 1.0 equiv.), 2,7-bis(4,4,5,5-tetramethyl-1,3,2-dioxaborolane-2-yl)-9H,9-dihexyldibenzosilole (100 mg, 0.17 mmol, 1.0 equiv.), palladium(II) acetate (1.0 mg, 45 μmol, 2.7%) and tricyclohexylphosphine (5 mg, 178 μmol, 10.7%) under nitrogen atmosphere. Dry toluene (2.5 cm³) was added and the mixture was stirred at 90° C. for 5 min. 20% w/w Tetraethylammonium hydroxide aqueous solution (1.0 cm³) was then added. The mixture was stirred for a further 2 h. To the mixture was then added phenylboronic acid (20.3 mg, 17 mmol, 1.0 equiv.), and after stirring for 1 h, bromobenzene (26.1 mg, 17 mmol, 1.0 equiv.) was added. After stirring for a further 1 h, the mixture was cooled to room temperature and poured into stirring methanol (30 cm$^3$). The precipitate was dissolved in toluene (10 cm$^3$) and reprecipitated in stirring methanol (50 cm$^3$). The precipitated product was filtered and then dried in vacuo to yield the title compound (90 mg, 78%) as a pale grayish green solid. GPC assay in CHCl$_3$ vs. narrow polystyrene standards revealed M$_w$=8.7×10$^4$, M$_n$=1.4×10$^4$, M$_p$=1.0× 10$^5$, PDI=7.41; ν$_{max}$/cm$^{-1}$ (Neat solid) 731, 820, 1062, 1248, 1408, 1447, 2854, 2920, 2955; δ$_H$(400 MHz, CDCl$_3$) 0.50-1.60 (m, CH$_2$+CH$_3$), 6.40-7.00 (brm, ArH), 7.40-8.10 (brm, ArH); δ$_C$(125 MHz, CDCl$_3$) 11.2, 14.1, 22.6, 24.6, 31.4, 33.1, 121.2, 129.0, 131.8, 138.8, 139.9, 147.2; δ$_{Si}$(100 MHz, CDCl$_3$) 3.07.

Polymer Example 2

A copolymer according to the invention was prepared by Suzuki polymerization as disclosed in WO 00/53656 with a diboronic acid of di(n-hexyl)fluorene followed by end-capping with bromobenzene and phenyl boronic acid to afford Polymer PS6F6 as shown below:

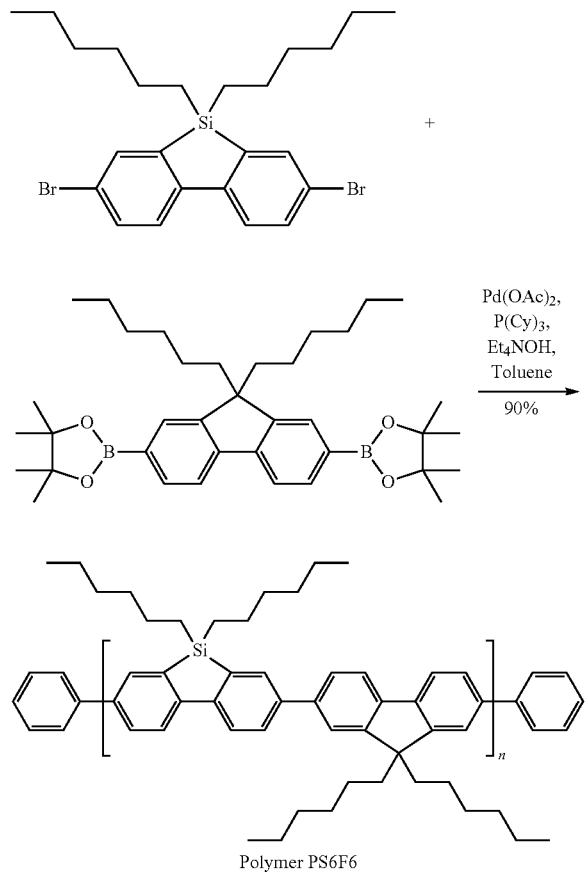

Polymer PS6F6

Poly(9,9-dihexyl-2,7-fluorenyl-alt-9,9-dihexyl-2,7-silafluorenyl)

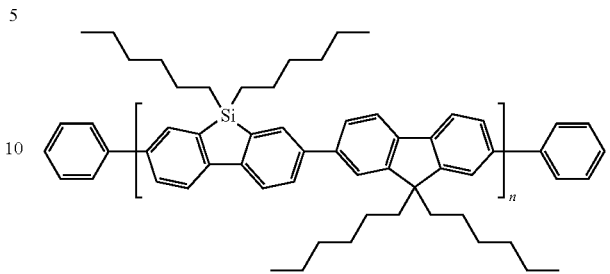

To a dried Schlenk tube was added 9,9-dihexyl-2,7-dibromo-9H-9-dibenzosilole (84 mg, 0.17 mmol, 1.0 equiv.), 2,7-bis(4,4,5,5-tetramethyl-1,3,2-dioxaborolane-2-yl)-9,9-dihexylfluorene (97 mg, 0.17 mmol, 1.0 equiv.), palladium (II) acetate (1.0 mg, 45 μmol, 2.7%) and tricyclohexylphosphine (5 mg, 178 μmol, 10.7%) under nitrogen atmosphere. Dry toluene (2.5 cm$^3$) was added and the mixture was stirred at 90° C. for 5 min. 20% w/w Tetraethylammonium hydroxide aqueous solution (1.0 cm$^3$) was then added. After 1 hour, the mixture became very viscous and additional dry toluene (1.0 cm$^3$) was added. The mixture was stirred for a further 1 h. To the mixture was then added phenylboronic acid (20.3 mg, 17 mmol, 1.0 equiv.), and after stirring for 1 h, bromobenzene (26.1 mg, 17 mmol, 1.0 equiv.) was added. After stirring for a further 1 h, the mixture was cooled to room temperature and poured into stirring methanol (30 cm$^3$). The precipitate was dissolved in toluene (10 cm$^3$) and reprecipitated in stirring methanol (50 cm$^3$). The precipitated product was filtered and then dried in vacuo to yield the title compound (100 mg, 93%) as a pale grayish green solid; GPC assay in CHCl$_3$ vs. narrow polystyrene standards revealed M$_w$=4.24×10$^5$, M$_n$=1.09×10$^5$, M$_p$=4.96×10$^5$, PDI=4.55; ν$_{max}$/cm$^{-1}$ (Neat solid) 734, 815, 1064, 1252, 1378, 1426, 1452, 2854, 2923, 2954; δ$_H$(500 MHz, CDCl$_3$) 0.74-0.89 (m, CH$_2$+CH$_3$), 1.00-1.20 (m, CH$_2$), 1.20-1.55 (m, CH$_2$), 2.10 (brs, CCH$_2$), 7.50-8.00 (m, ArH); δ$_C$(125 MHz, CDCl$_3$) 12.4, 14.0, 14.1, 22.56, 22.59, 23.8, 24.0, 29.7, 31.4, 31.5, 33.1, 40.4, 55.3, 120.0, 121.2, 121.4, 125.3, 128.2, 129.2, 131.9, 138.9, 140.1 (2 signals), 140.3, 147.1, 151.7; δ$_{Si}$(100 MHz, CDCl$_3$) 3.02.

Device Example

General Method: Onto indium tin oxide supported on a glass substrate (available from Applied Films, Colorado, USA) was deposited a layer of PEDT/PSS, available from H C Starck of Leverkusen, Germany as Baytron P®, by spin coating. A layer of electroluminescent polymer was deposited over the PEDT/PSS layer by spin-coating from xylene solution. Onto the layer of electroluminescent polymer was deposited by evaporation a cathode consisting of a first layer of calcium and a second, capping layer of aluminium.

Devices according to the invention were made according to the above method using Polymer PS6 and Polymer PS6F6.

For the purpose of comparison, a device was made according to the above method comprising a layer of poly-9,9-di(n-hexyl)-2,7-fluorene (hereinafter referred to as Polymer PF6).

As can be seen from the table below, the PS6 homopolymer according to the invention has a deeper LUMO level, i.e. it has a higher electron affinity, than the corresponding polyfluorene homopolymer PF6. At the same time, a wide HOMO-LUMO bandgap similar to that of PF6 is preserved. Furthermore, data for the PF6S6 polymer shows that a deep LUMO level is preserved when the dibenzosilole units of the invention are conjugated with units having a shallower LUMO level.

| Polymers | $E_{onset(ox)}$ (V)[a] | $E_g^{opt}$ (eV)[b] | HOMO (eV)[c] | LUMO (eV)[d] |
|---|---|---|---|---|
| PF6 | 1.41 | 2.93 | −5.84 | −2.91 |
| PF6S6 | 1.48 | 2.92 | −5.91 | −2.99 |
| PS6 | 1.52 | 2.93 | −5.95 | −3.02 |

[a]Oxidative onset potential.
[b]Optical band gap energy determined by the onset absorption (UV-Vis).
[c]Determined from $E_{onset(ox)}$ (taking energy level of ferrocene to be −4.8 eV under vacuum).
[d]Determined from adding $E_g^{opt}$ to the HOMO energy level.

Figure 2A:
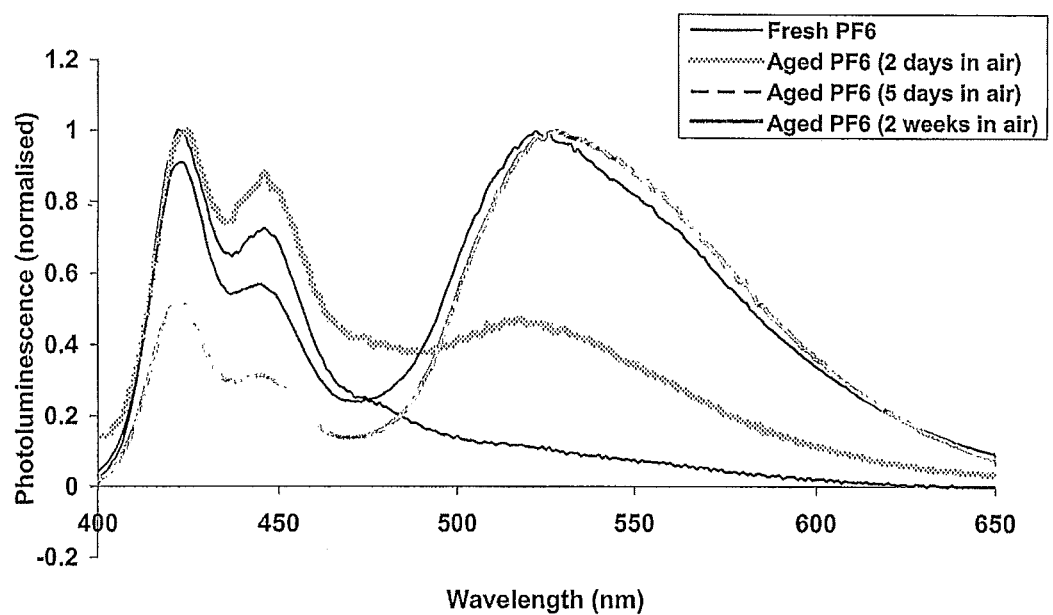
FIG. 2(a) shows a plot of photoluminescent wavelength over time for a prior art polyfluorene
Figure 2B:
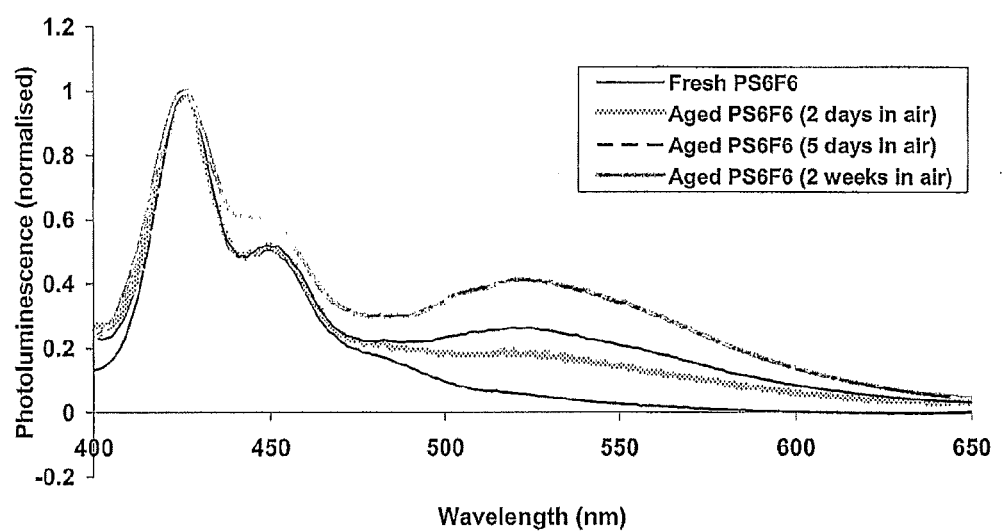
FIG. 2(b) shows a plot of photoluminescent wavelength over time for a co-polymer according to the invention
Figure 2C:
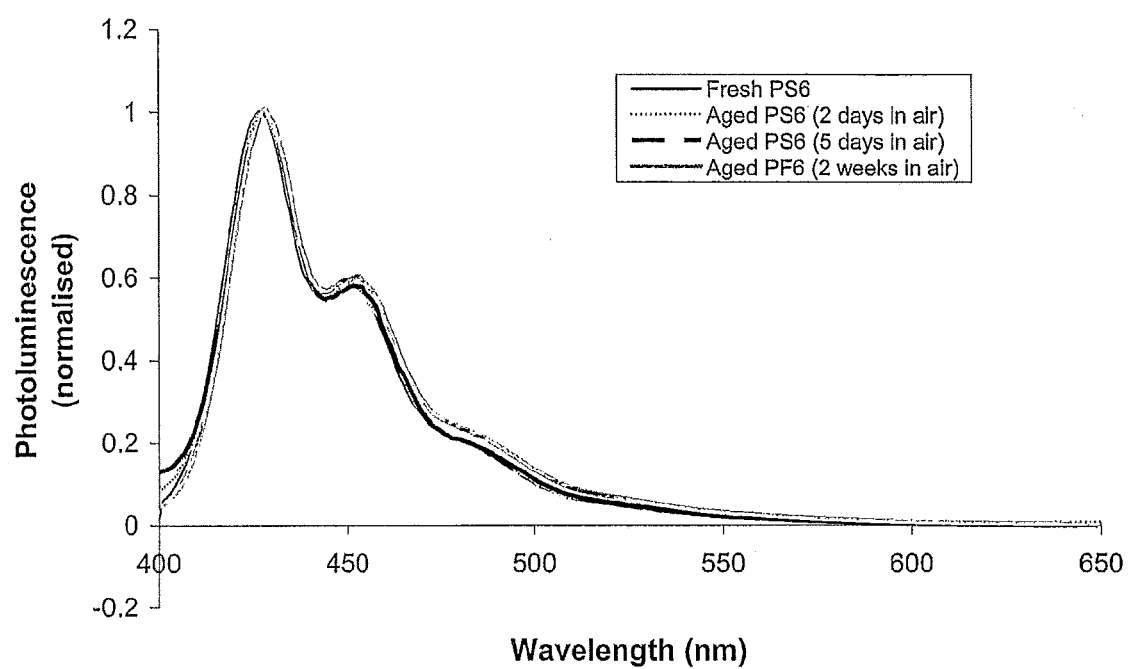
FIG. 2(c) shows a plot of photoluminescent wavelength over time for a homopolymer according to the invention

As can be seen from FIG. 2(a), photoluminescence of the prior art PF6 polymer suffers from very significant color shift over time towards the red end of the visible spectrum. Incorporation of dibenzosilole repeat units into the PF6 polymer, as shown in FIG. 2(b), results in a very significant reduction in this color shift, and color shift for the S6 homopolymer, as shown in FIG. 2(c), is negligible.

Figure 3:
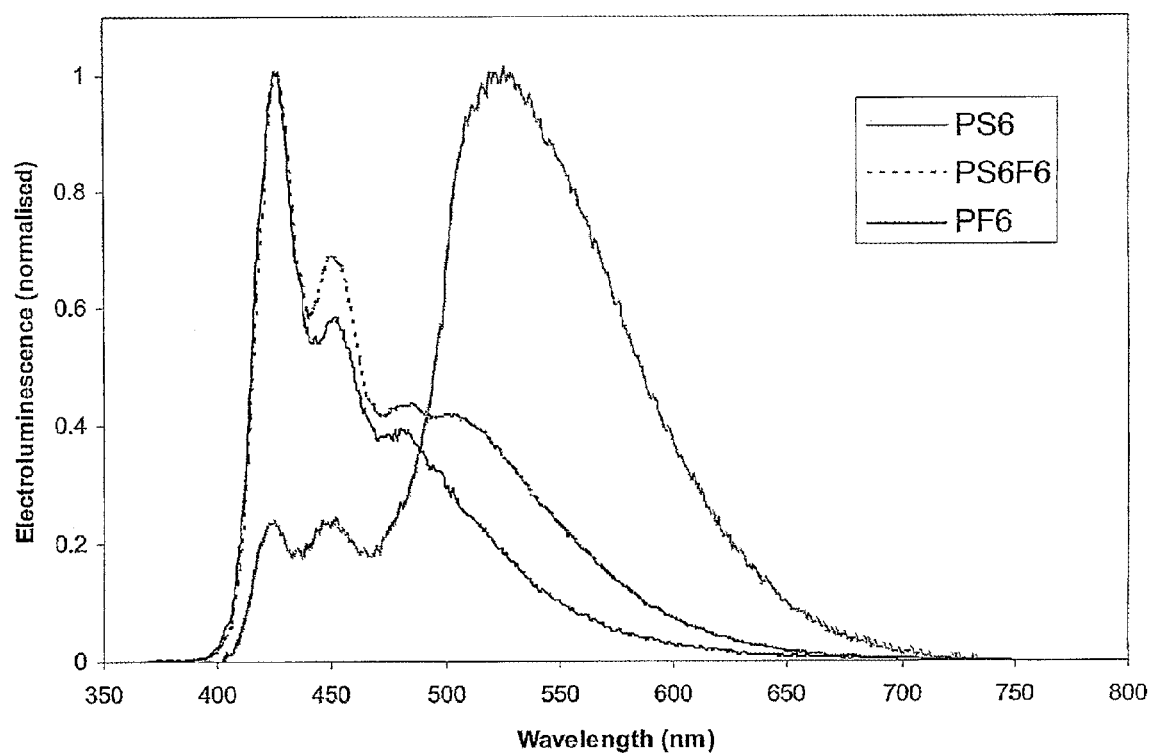
FIG. 3 shows a plot of electroluminescent wavelength for polymers according to the invention as compared to a prior art polyfluorene

As can be seen from FIG. 3, devices comprising PS6 or PS6F6 give sustained blue emission with emission maxima being identical to that of photoluminescence at 426 nm. The PF6 device on the other hand degraded very rapidly under current and showed a green emission upon operation, displaying a broad peak at about 540 nm.

B) 3,6-Linked Dibenzosilole Monomers and Repeat Units

A monomer according to the ninth aspect of the invention was synthesised according to the following reaction scheme. Again, as with the 2,7-linked dibenzosiloles described above, transalkylation of the dimethylsilyl group (step e) does not affect the trimethylsilyl end groups and so this route again provides a means for introducing a wide range of substituents on the silicon atom.

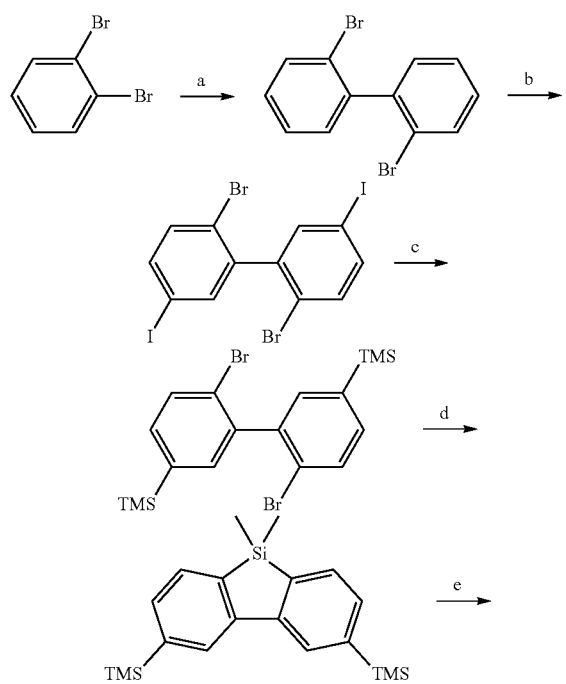

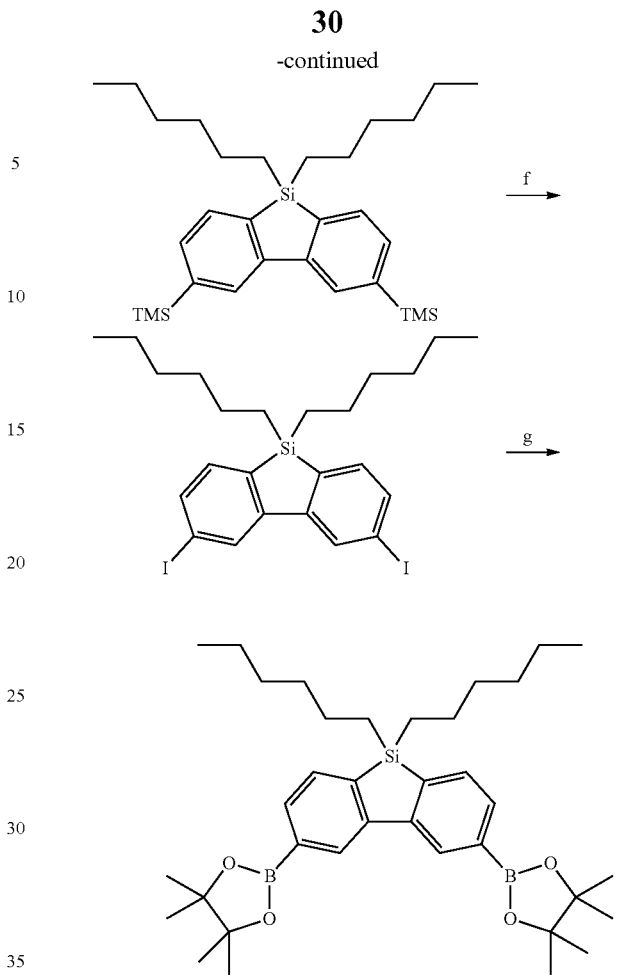

Scheme Synthesis of dibenzosilole monomers: a) n-BuLi, THF, −78° C. to rt, 24 h, 88%; b) I$_2$, NaIO$_4$, conc. H$_2$SO$_4$, AcOH, Ac$_2$O, 24 h, 40%; c) n-BuLi, TMSCl, −78° C. to rt, 24 h, 84%; d) (i) t-BuLi, −78° C. to rt, 24 h (ii) SiMe$_2$Cl$_2$, −78° C. to rt, 24 h, 81%; e) n-HexLi, −78° C., 15 min, 95%; f) ICl, DCM, r.t., 1 h, 90%; g) t-BuLi, 2-isopropoxy-4,4',5,5'-tetramethyl-1,3,2-dioxaboralane, −78° C. to rt, 24 h.

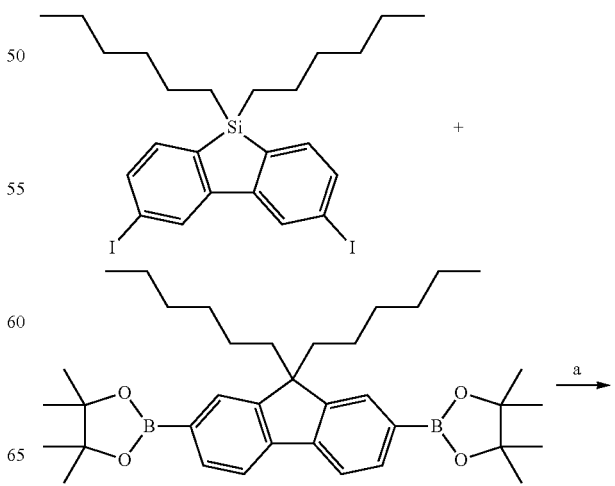

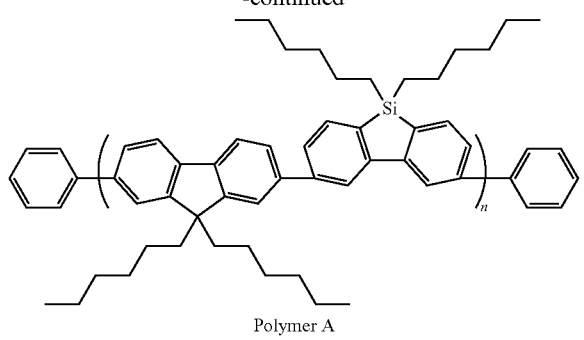

Polymer A

Scheme a) (1) P(OAc)$_2$, P(Cy)$_3$, Et$_4$NOH, Toluene, 90° C., 24 h (ii) phenylboronic acid, 2 h (iii) bromobenzene, 2 h, 51%.

For the purpose of comparison, the 2,7-linked polymer poly(9,9-dihexyl-2,7-fluorenyl-alt-9,9-dihexyl-2,7-dibenzosilyl) (Polymer B) was prepared.

Poly(9,9-dihexyl-2,7-fluorenyl-alt-9,9-dihexyl-3,6-dibenzosilyl) (Polymer A) was prepared according to the following method:

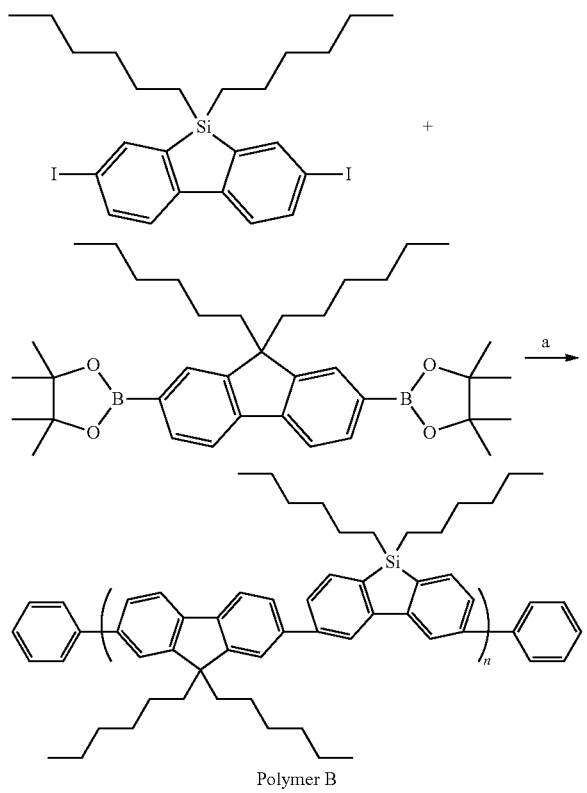

Polymer B

Scheme a) (i) P(OAc)$_2$, P(Cy)$_3$, Et$_4$NOH, Toluene, 90° C., 24 h (ii) phenylboronic acid, 2 h (iii) bromobenzene, 2 h, 90%.

UV-Vis absorption spectra

The table below shows the absorption maxima and optical band gaps of the copolymers. The solution UV-Vis absorption spectra of the copolymers were measured in hexane.

| Polymer | $\lambda_{max}$ (nm)[a] | | $E_g^{opt}$ (eV, nm)[b] | |
|---|---|---|---|---|
| | solution | film | solution | film |
| PF6 | 394 | 390 | 2.98 (416) | 2.93 (423) |
| Polymer A | 332 | 334 | 3.30 (376) | 3.23 (383) |
| Polymer B | 400 | 394 | 2.87 (432) | 2.92 (425) |

[a]Optical band gap, $E_g^{opt}$ (eV) = 1240/absorption edge (nm).
[b]Band gaps of the polymers, measured from the UV absorption onsets.

As can be seen from the table, Polymer A comprising a 3,7-linked dibenzosilole according to the eighth aspect of the invention is significantly blue shifted and has a wider bandgap as compared to the 2,7-linked poly-dibenzosilole Polymer B and the 2,7-linked polyfluorene PF6.

Cyclic Voltammetry

The films of the copolymers were prepared by spin-coating the samples (1.0 wt % solution in toluene) on the gold working electrode. Measurements were then taken in a solution of Bu$_4$N$^+$ClO$_4^-$ (0.10 M) in acetonitrile at a scan rate of 50 mV/s at room temperature, using a platinum wire as the counter electrode and a Ag/AgCl electrode as the reference electrode. Both measurements were calibrated against ferrocene which has an ionization potential of 4.8 eV.

As can be seen from the table below, the 3,6-linked polydibenzosilole of Polymer A according to the eighth aspect of the invention has a wider HOMO-LUMO bandgap as compared to 2,7-linked Polymer A.

| Polymers | $E_{onset(ox)}$ (V)[a] | $E_g^{opt}$ (eV)[b] | HOMO (eV)[c] | LUMO (eV)[d] |
|---|---|---|---|---|
| Polymer A | 1.57 | 3.23 | −6.00 | −2.77 |
| Polymer B | 1.48 | 2.92 | −5.91 | −2.99 |

[a]Oxidative onset potential.
[b]Optical band gap energy determined by the onset absorption (UV-Vis).
[c]Determined from $E_{onset(ox)}$ (taking energy level of ferrocene to be −4.8 eV under vacuum).
[d]Determined from adding $E_g^{opt}$ to the HOMO energy level.

Although the present invention has been described in terms of specific exemplary embodiments, it will be appreciated that various modifications, alterations and/or combinations of features disclosed herein will be apparent to those skilled in the art without departing from the spirit and scope of the invention as set forth in the following claims.

The invention claimed is:
1. A composition comprising:
a polymer comprising an optionally substituted first repeat unit of formula (VII):

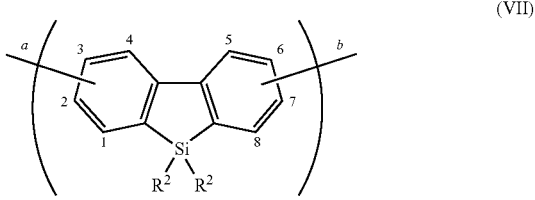

(VII)

wherein each R$^2$ is the same or different and represents a substituent; the R$^2$ groups may be linked to form a ring; bond (a) is bound to the 3-position of the repeat unit of formula (VII); and bond (b) is bound to the 6-position of the repeat unit of formula (VII); and,
a phosphorescent dopant.

2. A composition according to claim 1, wherein at least one $R^2$ is a solubilizing group.

3. A composition according to claim 1, wherein each $R^2$ is the same or different and is selected from the group consisting of optionally substituted $C_{1-20}$ alkyl, optionally substituted $C_{1-20}$ alkoxy, optionally substituted aryl, and optionally substituted heteroaryl.

4. A composition according to claim 3, wherein each $R^2$ is a $C_4$-$C_{10}$ alkyl.

5. A composition according to claim 1 wherein the polymer comprises an optionally substituted aryl or heteroaryl second repeat unit.

6. An optionally substituted monomer of formula (VIII):

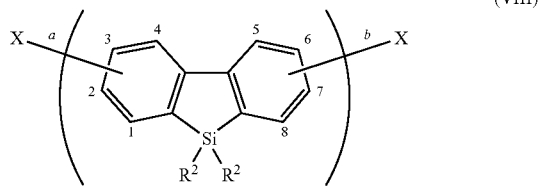

(VIII)

wherein each $R^2$ is the same or different and represents a substituent; each X independently represents a polymerizable group; bond (a) is bound to the 3-position of the repeat unit of formula (VII); and bond (b) is bound to the 6-position of the repeat unit of formula (VII).

7. A monomer according to claim 6, wherein each $R^2$ is the same or different and is selected from the group consisting of optionally substituted $C_{1-20}$ alkyl, optionally substituted $C_{1-20}$ alkoxy, optionally substituted aryl, and optionally substituted heteroaryl.

8. A monomer according to claim 6, wherein each $R^2$ is a $C_4$-$C_{10}$ alkyl.

9. An electroluminescent device comprising an anode, a cathode and an electroluminescent layer located between the anode and cathode wherein the electroluminescent layer comprises a polymeric host material comprising an optionally substituted first repeat unit of formula (VII) and a phosphorescent dopant:

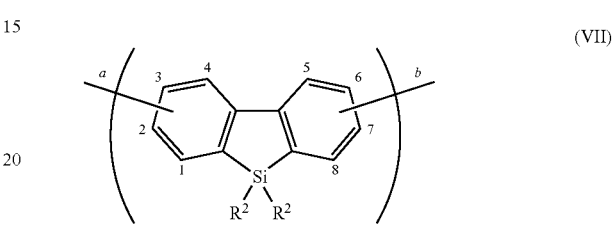

(VII)

wherein each $R^2$ is the same or different and represents a substituent; the $R^2$ groups may be linked to form a ring; bond (a) is bound to the 3-position of the repeat unit of formula (VII); and bond (b) is bound to the 6-position of the repeat unit of formula (VII).

* * * * *